(12) United States Patent
Stössel et al.

(10) Patent No.: US 7,589,203 B2
(45) Date of Patent: Sep. 15, 2009

(54) RHODIUM AND IRIDIUM COMPLEXES

(75) Inventors: Philipp Stössel, Frankfurt am Main (DE); Hubert Spreitzer, Viernheim (DE); Ingrid Bach, Bad Soden (DE)

(73) Assignee: Merck Patent GmbH, Darmstadt (DE)

( * ) Notice: Subject to any disclaimer, the term of this patent is extended or adjusted under 35 U.S.C. 154(b) by 636 days.

(21) Appl. No.: 10/532,185

(22) PCT Filed: Sep. 25, 2003

(86) PCT No.: PCT/EP03/10652

§ 371 (c)(1),
(2), (4) Date: Jul. 6, 2005

(87) PCT Pub. No.: WO2004/037836

PCT Pub. Date: May 6, 2004

(65) Prior Publication Data

US 2005/0253135 A1 Nov. 17, 2005

(30) Foreign Application Priority Data

Oct. 26, 2002 (DE) .............................. 102 49 926

(51) Int. Cl.
*C07F 15/00* (2006.01)
*C07F 5/06* (2006.01)

(52) U.S. Cl. ............... 546/2; 546/4; 549/3; 549/206
(58) Field of Classification Search ............... 546/2, 546/4; 549/3, 206
See application file for complete search history.

(56) References Cited

FOREIGN PATENT DOCUMENTS

EP 1 191 613 A2 3/2002
JP 2003 073387 A 3/2003

OTHER PUBLICATIONS

Selbin et al., Journal of Organometallic Chemistry, vol. 214, pp. 253-259 (1981).*

* cited by examiner

*Primary Examiner*—Porfirio Nazario Gonzalez
(74) *Attorney, Agent, or Firm*—Hamilton, Brook, Smith & Reynolds, P.C.

(57) ABSTRACT

The present invention relates to novel organometallic compounds which are phosphorescence emitters. Such compounds can be used as active components (=functional materials) in a series of different types of application which can be classed within the electronics industry in the broadest sense.

The inventive compounds are described by the formulae (1) to (32) and (1*a*) to (8*a*).

7 Claims, No Drawings

RHODIUM AND IRIDIUM COMPLEXES

RELATED APPLICATIONS

This application is the U.S. National Stage of International Application No. PCT/EP2003/010652, filed Sep. 25, 2003, published in German, and claims priority under 35 U.S.C. § 119 or 365 to German Application No. 102 49 926.8, filed Oct. 26, 2002.

Organometallic compounds, especially compounds of the $d^8$ metals, will find use as functional components in the near future as active components (=functional materials) in a series of different types of application which can be classed within the electronics industry in the broadest sense.

The organic electroluminescent devices based on organic components (for a general description of the construction, see U.S. Pat. Nos. 4,539,507 and 5,151,629) and their individual components, the organic light-emitting diodes (OLEDs), have already been introduced onto the market, as demonstrated by the available car radios having organic displays from Pioneer. Further products of this type will shortly be introduced. In spite of this, distinct improvements are still necessary here for these displays to provide real competition to the currently market-leading liquid crystal displays (LCDs) or to overtake them.

A development in this direction which has emerged in recent years is the use of organometallic complexes which exhibit phosphorescence instead of fluorescence [M. A. Baldo, S. Lamansky, P. E. Burrows, M. E. Thompson, S. R. Forrest, Applied Physics Letters, 1999, 75, 4-6].

For theoretical reasons relating to the spin probability, up to four times the energy efficiency and performance efficiency are possible using organometallic compounds as phosphorescence emitters. Whether this new development will establish itself depends strongly upon whether corresponding device compositions can be found which can also utilize these advantages (triplet emission=phosphorescence compared to single emission=fluorescence) in OLEDs. The essential conditions for practical use are in particular a long operative lifetime, a high stability against thermal stress and a low use and operating voltage, in order to enable mobile applications.

In addition, there has to be efficient chemical access to the corresponding organometallic compounds. Of particular interest in this context are organorhodium and organoiridium compounds. Especially taking into account the cost of rhodium and iridium, it is of crucial importance here that efficient access to the corresponding derivatives is enabled.

Mono-, di-, tri-, tetra- and hexa-nitro-functionalized bis- and tris-ortho-metalated organorhodium and organoiridium compounds [as per compounds (1) to (32) and (1a) to (8a)], which form the subject matter of the present invention, are central key building blocks for obtaining highly efficient triplet emitters, since the nitrofunction can be converted with the aid of common methods described in the literature to a multitude of functions (for example the amino, nitroso, hydroxylamino, azo and the azoxy function). It is thus possible not only to covalently incorporate these active, light-emitting centers into a multitude of polymers, but also to tailor the optoelectronic properties of these building blocks. For instance, typical reduction reactions starting from the nitro compounds lead to the abovementioned amino, nitroso, hydroxylamino, azo and the azoxy compounds which can then either be further functionalized in C—N bond-forming reactions (for example imine formation or Hartwig-Buchwald coupling) or be used as (co)monomers in the preparation of corresponding polymers.

Mono-, di-, tri-, tetra- and hexa-nitro-functionalized bis- and tris-ortho-metalated organo-rhodium and organoiridium compounds have not been described to date in the literature, but their efficient preparation and availability as pure substances is of great importance for various electrooptical applications.

Even though the above remarks describe mainly use of the inventive mono-, di-, tri-, tetra- and hexa-nitro-functionalized bis- and tris-ortho-metalated organorhodium and organoiridium compounds in OLEDs, it should be pointed out that these compounds may likewise very readily find use in the following devices:

1. Use in photovoltaic devices such as organic photodetectors or organic solar cells, for example as an electron acceptor or transport material.
2. Use in organic integrated circuits (O-ICs).
3. Use in organic field-effect transistors (OFETs).
4. Use in organic thin-film transistors (OTFTs).
5. Use in organic solid-state lasers.

The closest prior art to the synthesis of the nitro compounds (1) to (32) may be regarded as being the nitration of uncharged ruthenium(II) or osmium(II) complexes which, in addition to the ortho-metalated 2-phenylpyridine or 2-(1'-naphthyl)pyridine or 2-phenylquinoline ligands, may also bear further monodentate ligands [A. M. Clark, C. E. F. Rickard, W. R. Roper, L. J. Wright Organometallics. 1999, 18, 2813-2820 and A. M. Clark, C. E. F. Rickard, W. R. Roper, L. J. Wright J, Organomet. Chem., 2000, 598, 262-275].

The nitrating agent used is copper(II) nitrate in acetic anhydride. After chromatographic purification, the corresponding nitrated products are obtained in yields of from 10 to 40%—in individual cases up to 87%.

These two references have the following disadvantages:
(1) Only the derivatization of Ru or Os complexes, but not those of Rh or Ir compounds is described.
(2) No sensible teaching is provided as to how, in the presence of a plurality of substitutable sites, the desired mono- or di- or tri-, tetra- or hexa-functionalized compounds are selectively obtained, since in both cases in each case only one nitration is possible in the para- or ortho-position to the metal atom per complex molecule.

In contrast, the mono-, di-, tri-, tetra- and hexa-nitration of bis- and tris-ortho-metalated organorhodium and organoiridium compounds has not been described to date in the literature.

It has now been found that, surprisingly, the novel compounds (1) to (32) according to schemes 1, 2, 3 and 4 can be obtained reproducibly in about 70-98% yield, without using chromatographic purification processes, optionally after recrystallization, in purities of >99% by NMR or HPLC starting from the bis- or tris-ortho-metalated organorhodium or organoiridium compounds (33) to (64) with a nitrating agent, with suitable selection of the stoichiometric ratio of the appropriate nitrating agent to the compounds (33) to (64) and with suitable selection of the reaction parameters such as reaction temperature, reaction medium, concentration and reaction times (see Example 1, 2 and 3).

The starting compounds (33) to (64) may be prepared partly by common literature methods, but in particular also according to the published or nonpublished applications WO 02/060910, DE 10223337.3, WO 02/068435, DE 10155064.2, DE 10223337.3, DE 10215010.9 and DE 10238903.9.

The above-described process is notable particularly for three properties which have not been described in this form in the literature to date:

Firstly, the selective mono-, di-, tri-, tetra- and hexa-nitration of bis- and tris-ortho-metalated rhodium and iridium compounds is unexpected and unknown in this form. It is thought to result from the activation that the para- and ortho-position(s) to the rhodium or iridium atom in the coordinated phenyl ring experience(s) as a result of this atom. The unexpectedly high activity of these positions with respect to an electrophilic substitution, nitration here, is exploited selectively by the use of mild nitration agents. In addition, a high selectivity of the nitration of the para-position to the metal in comparison to the ortho-substitution which is likewise possible is found, i.e. in a given molecule, all para-positions are always nitrated first before the nitration proceeds in the ortho-positions under suitable conditions.

Secondly, the high conversion achieved, which is reflected in the reproducibly very good yields of isolated product, is unexpected and unique for the nitration of ortho-metalated ligands bonded to metals of the 9th group.

Thirdly, the resulting compounds, optionally after recrystallization but without costly and inconvenient chromatographic purification, are obtained in very good yields of >99% by NMR or HPLC. This is essential for use in optoelectronic components, and utilization as intermediates for the preparation of corresponding compounds.

As outlined above, the inventive compounds have not been described before and are thus novel.

The present invention provides the tris-ortho-metalated compounds (1) to (8) according to scheme 1:

Scheme 1:

Compounds (1)

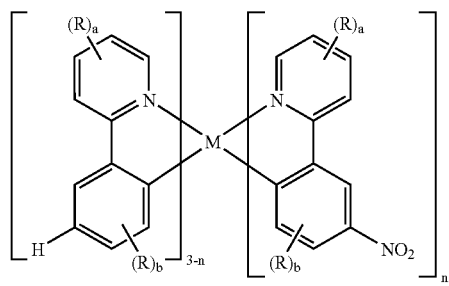

Compounds (2)

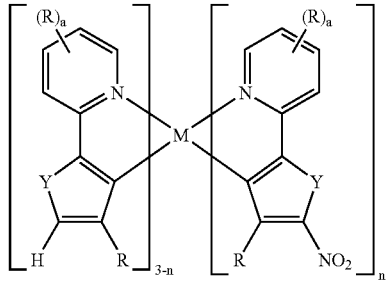

-continued

Compounds (3)

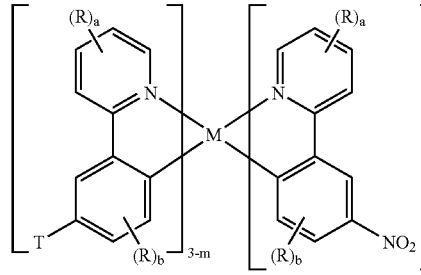

Compounds (4)

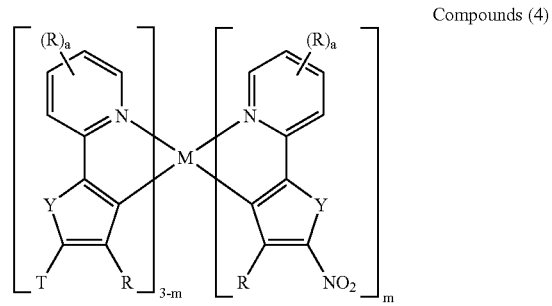

Compounds (5)

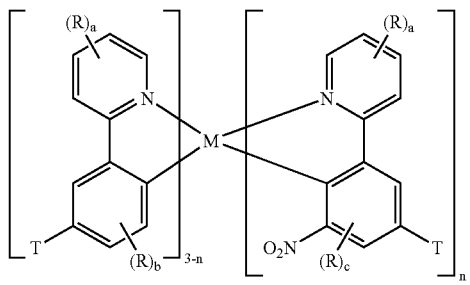

Compounds (6)

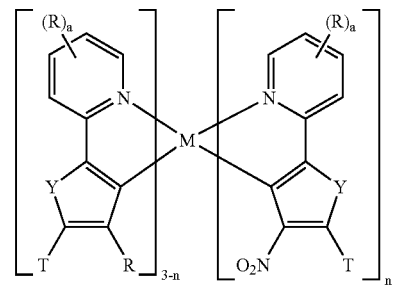

Compounds (7)

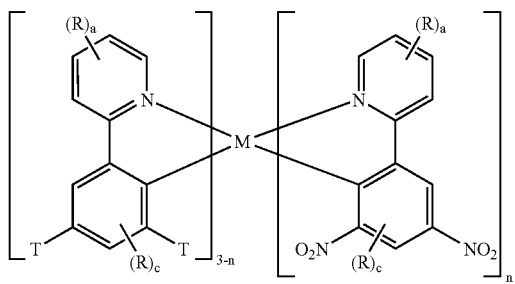

Compounds (8)

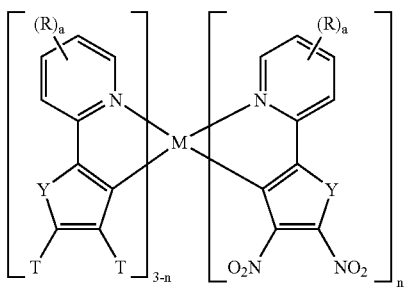

where the symbols and indices are each defined as follows:
M is Rh, Ir;
Y is O, S, Se, $NR^1$;
R is the same or different at each instance and is H, F, Cl, Br, CN, a straight-chain or branched or cyclic alkyl or alkoxy group having from 1 to 20 carbon atoms, in which one or more nonadjacent $CH_2$ groups may be replaced by —O—, —$SiR^1_2$—, —S—, —$NR^1$— or —$CONR^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

T is the same or different at each instance and is F, Cl, Br, CN, a straight-chain or branched or cyclic alkyl or alkoxy group having from 1 to 20 carbon atoms, in which one or more nonadjacent $CH_2$ groups may be replaced by —O—, —$SiR^1_2$—, —S—, —$NR^1$— or —$CONR^1$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

$R^1$ is the same or different at each instance and is H or an aliphatic or aromatic hydrocarbon radical having from 1 to 20 carbon atoms;
a is 0, 1, 2, 3 or 4, preferably 0, 1 or 2;
b is 0, 1, 2 or 3, preferably 0 or 1;
c is 0, 1 or 2;
m is 1 or 2;
n is 1, 2 or 3.

In the case of the compounds (1) to (8), preference is given to the homoleptic compounds.

A further embodiment of the invention is those Rh or Ir complexes which simultaneously have ligands of the type such as in the compounds (1) and those of compounds (2), i.e. mixed ligand systems. These are described by the compounds (1a) to (8a) according to scheme 2:

Scheme 2:

Compounds (1a)

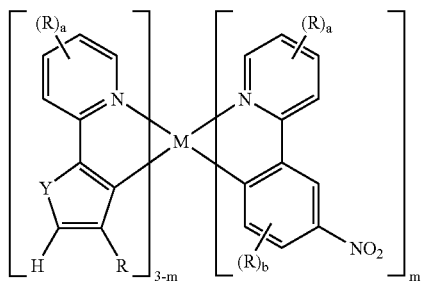

Compounds (2a)

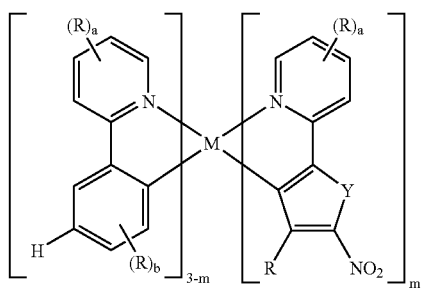

Compounds (3a)

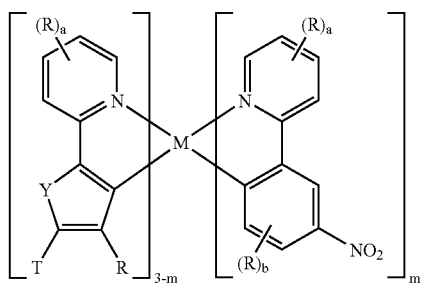

Compounds (4a)

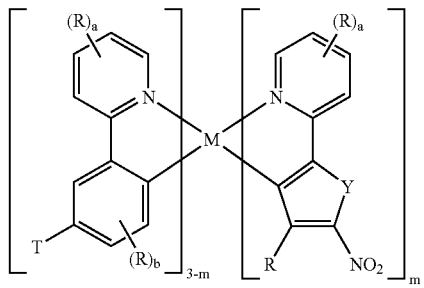

-continued
Compounds (5a)
Compounds (6a)
Compounds (7a)
Compounds (8a)
where the symbols and indices are each as defined under the compounds (1) to (8).
The present invention likewise provides the heteroleptic, bis-ortho-metalated compounds (9) to (16) according to scheme 3,
Scheme 3
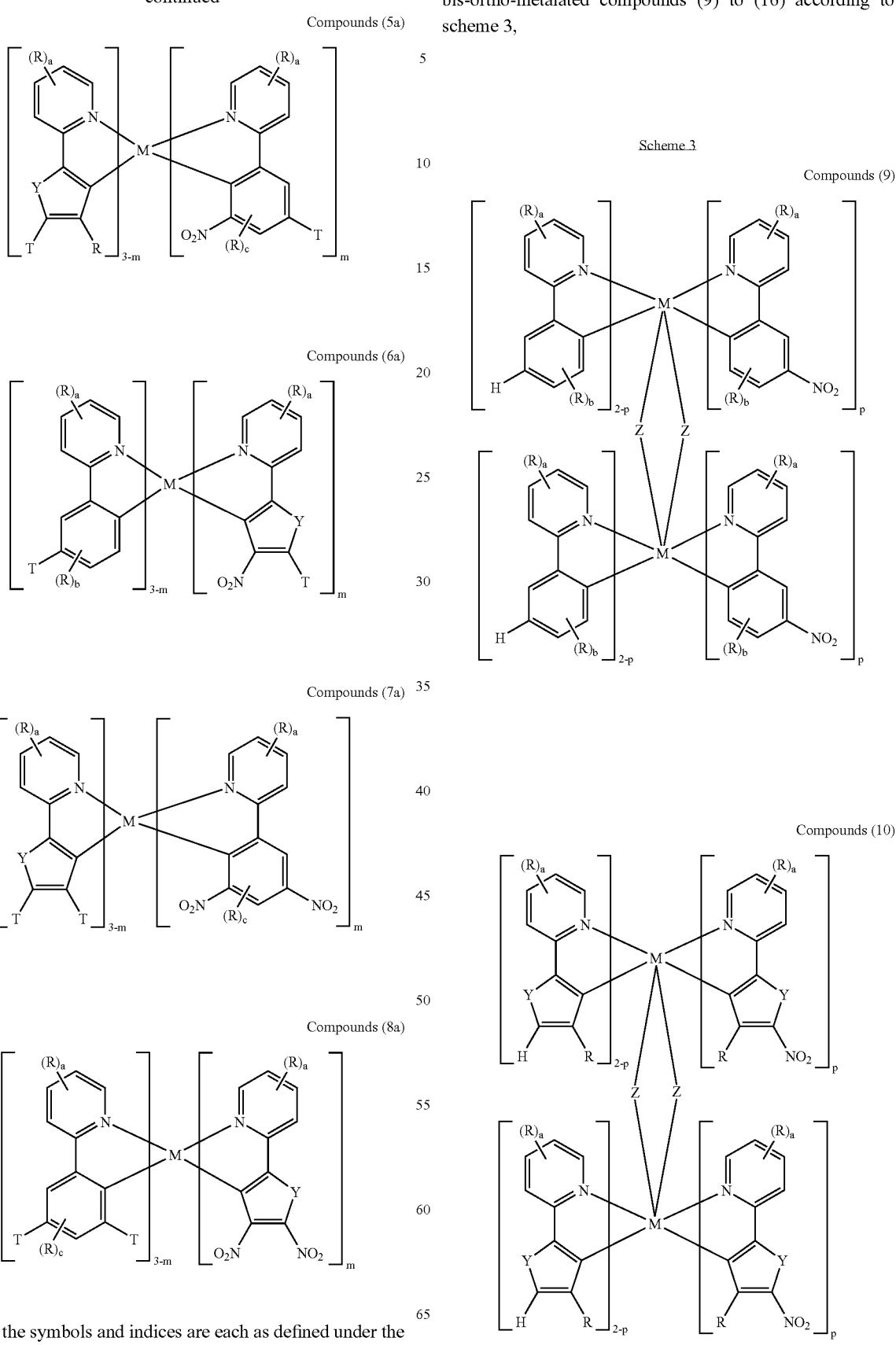
Compounds (9)
Compounds (10)

Compounds (11)
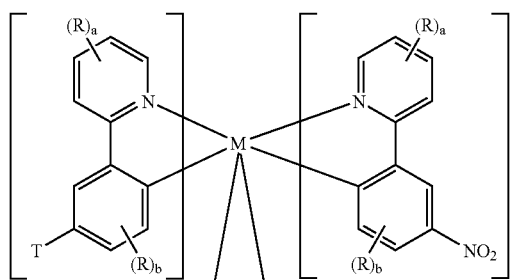
Compounds (12)
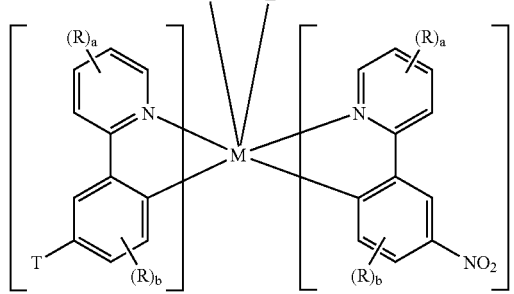
Compounds (13)
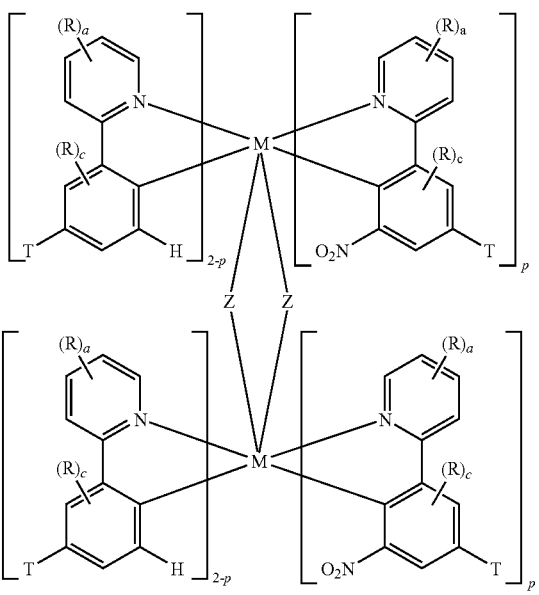
Compounds (14)
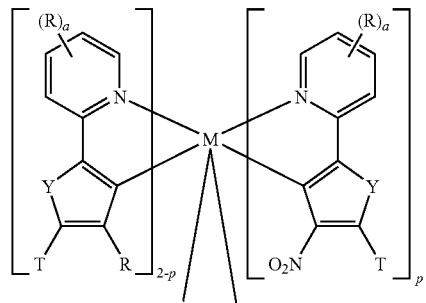
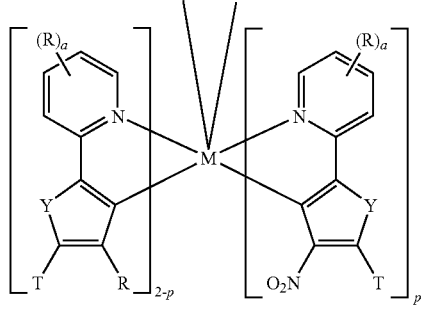

-continued

Compounds (15)

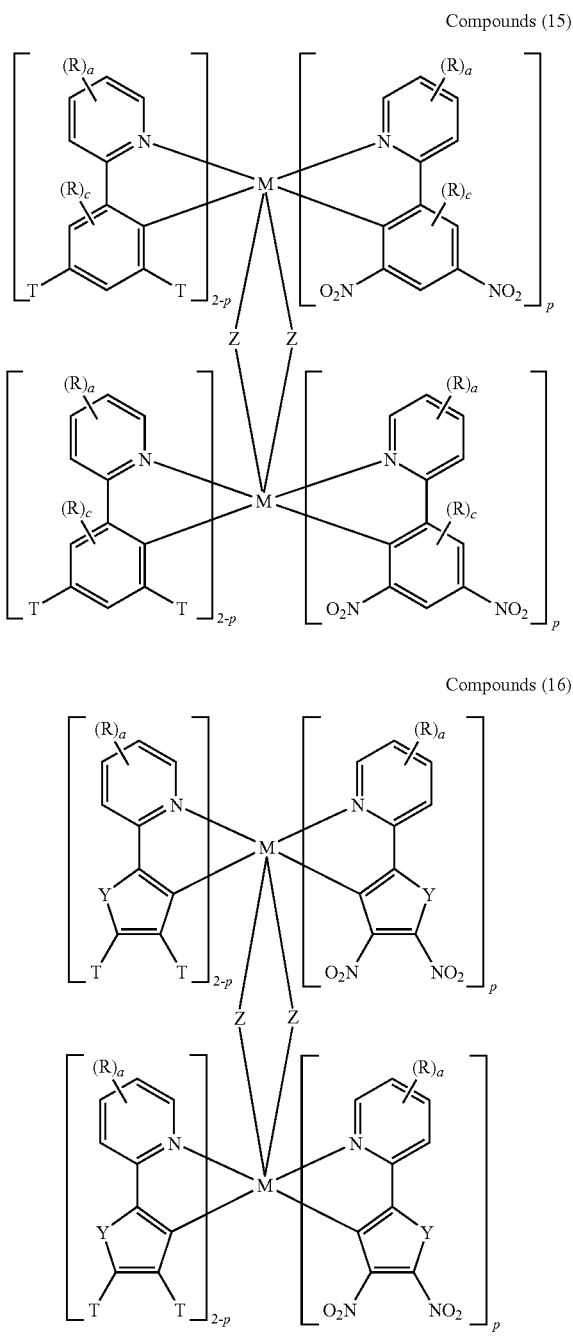

Compounds (16)

where the symbols and indices are each defined as follows:

M is Rh, Ir;

Y is O, S, Se, $NR^1$;

Z is F, Cl, Br, I, O—$R^1$, S—$R^1$, $N(R^1)_2$;

R is the same or different at each instance and is H, F, Cl, Br, CN, a straight-chain or branched or cyclic alkyl or alkoxy group having from 1 to 20 carbon atoms, in which one or more nonadjacent $CH_2$ groups may be replaced by —O—, —$SiR^1_2$—, —S—, —$NR^1$— or —$CONR^2$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

T is the same or different at each instance and is F, Cl, Br, CN, a straight-chain or branched or cyclic alkyl or alkoxy group having from 1 to 20 carbon atoms, in which one or more nonadjacent $CH_2$ groups may be replaced by —O—, —$SiR^1_2$—, —S—, —$NR^1$— or —$CONR^2$— and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

$R^1$ is the same or different at each instance and is H or an aliphatic or aromatic hydrocarbon radical having from 1 to 20 carbon atoms;

a is 0, 1, 2, 3 or 4, preferably 0, 1 or 2;

b is 0, 1, 2 or 3, preferably 0 or 1;

c is 0, 1 or 2;

p is 1 or 2.

The present invention likewise provides the heteroleptic, bis-ortho-metalated compounds (17) to (32) according to scheme 4:

Scheme 4:

Compounds (17)

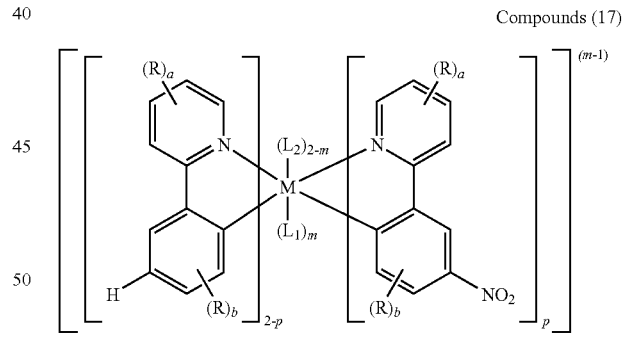

Compounds (18)

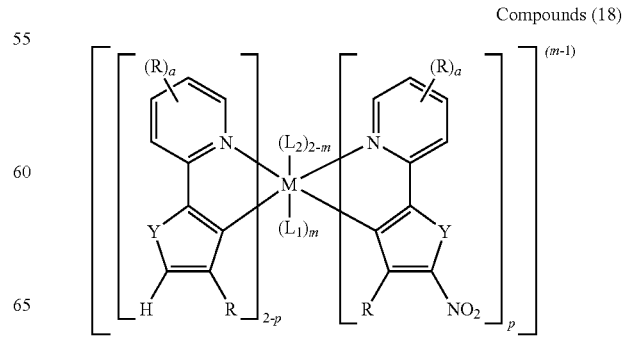

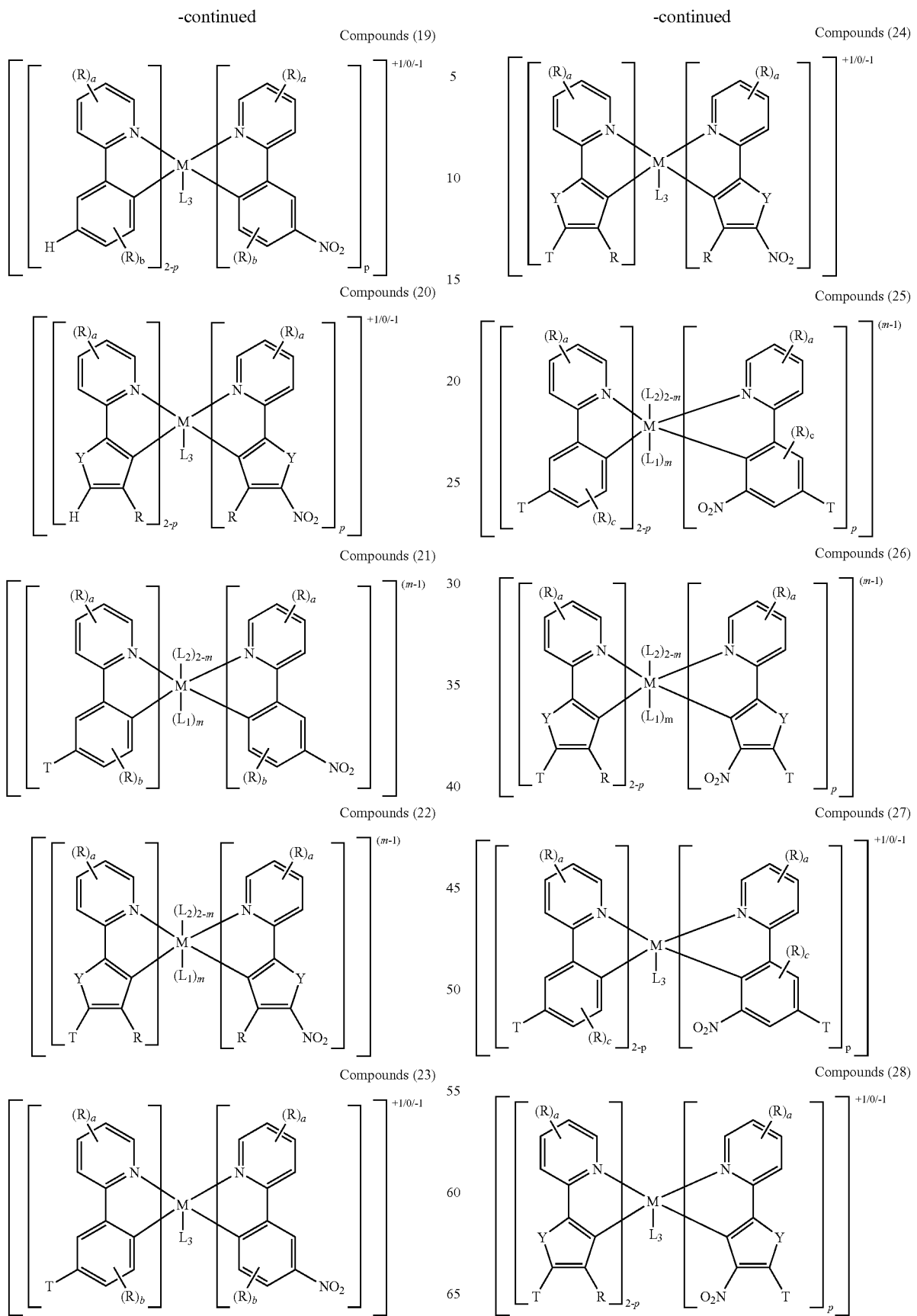

-continued

Compounds (29)

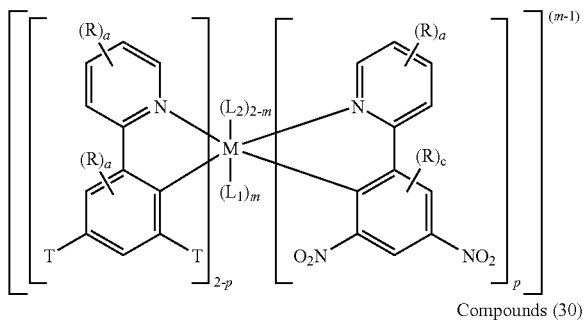

Compounds (30)

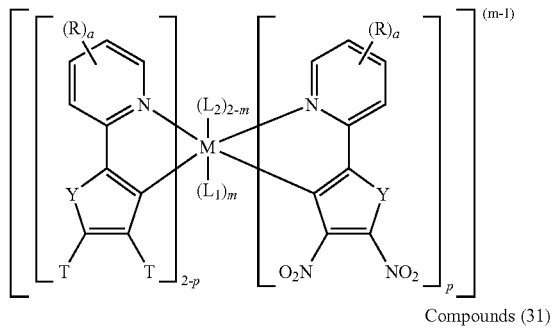

Compounds (31)

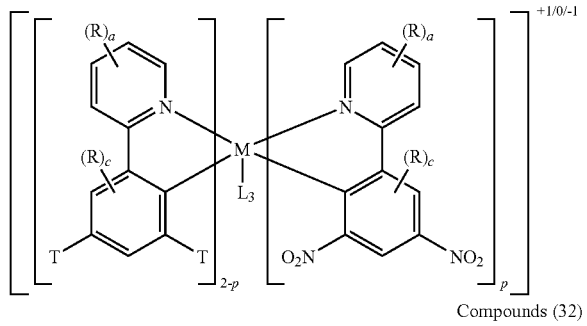

Compounds (32)

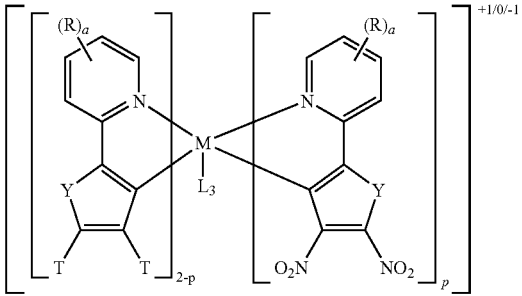

where the symbols and indices are each defined as follows:

M is Rh, Ir,

Y is O, S, Se, $NR^1$;

R is the same or different at each instance and is H, F, Cl, Br, CN, a straight-chain or branched or cyclic alkyl or alkoxy group having from 1 to 20 carbon atoms, in which one or more nonadjacent $CH_2$ groups may be replaced by —O—, —S—, $—NR^1—$ or $—CONR^2—$ and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

T is the same or different at each instance and is F, Cl, Br, CN, a straight-chain or branched or cyclic alkyl or alkoxy group having from 1 to 20 carbon atoms, in which one or more nonadjacent $CH_2$ groups may be replaced by —O—, $—SiR^1_2—$, —S—, $—NR^1—$ or $—CONR^2—$ and in which one or more hydrogen atoms may be replaced by F, or an aryl or heteroaryl group having from 4 to 14 carbon atoms which may be substituted by one or more nonaromatic R radicals, and a plurality of R substituents, either on the same ring or on the two different rings, may together in turn form one further aliphatic or aromatic, mono- or polycyclic ring system;

$R^1$ is the same or different at each instance and is H or an aliphatic or aromatic hydrocarbon radical having from 1 to 20 carbon atoms;

$L_1$ is an uncharged, monodentate ligand;

$L_2$ is a monoanionic, monodentate ligand;

$L_3$ is an uncharged or mono- or dianionic bidentate ligand;

a is 0, 1, 2, 3 or 4, preferably 0, 1 or 2;

b is 0, 1, 2 or 3, preferably 0 or 1;

m is 0, 1 or 2;

p is 1 or 2.

Inventive uncharged monodentate ligands $L_1$ are carbon monoxide, isonitriles, for example tert-butylisonitrile, cyclohexylisonitrile, adamantylisonitrile, amines, for example trimethylamine, triethylamine, morpholine, phosphines, for example trifluorophosphine, trimethylphosphine, tricyclohexylphosphine, tri-tert-butylphosphine, triphenylphosphine, tris(pentafluorophenyl)phosphine, phosphites, for example trimethyl phosphite, triethyl phosphite, arsines, for example trifluoroarsine, trimethylarsine, tricyclohexylarsine, tri-tert-butylarsine, triphenylarsinine, tris(pentafluorophenyl)arsine, stibines, for example trifluorostibine, trimethylstibine, tricyclohexylstibine, tri-tert-butylstibine, triphenylstibine, tris(pentafluorophenyl)stibine and nitrogen heterocycles, for example pyridine, pyridazine, pyrazine, triazine.

Inventive monoanionic monodentate ligands $L_2$ are the halides F, Cl, Br, I, and cyanide, cyanate, isocyanate, thiocyanate, isothiocyanate, alkoxides, for example methoxide, ethoxide, propoxide, isopropoxide, tert-butoxide, phenoxide, thioalkoxides, for example methanethiolate, ethanethiolate, propanethiolate, isopropanethiolate, tert-thiobutoxide, thiophenoxide, amides, for example dimethylamide, diethylamide, diisopropylamide, morpholide, carboxylates, for example acetate, trifluoroacetate, propionate, benzoate, and anionic nitrogen heterocycles such as pyrrolide, imidazolide, pyrazolide.

Inventive uncharged or mono- or dianionic bidentate ligands $L_3$ are diamines, for example ethylenediamine, N,N,N',N'-tetramethylethylenediamine, propylenediamine, N,N,N',N'-tetramethylpropylenediamine, cis-, trans-diaminocyclohexane, cis-, trans-N,N,N',N'-tetramethyldiaminocyclohexane, imines, for example 2[(1-(phenylimino)ethyl]pyridine, 2[(1-(2-methylphenylimino)ethyl]pyridine, 2[(1-(2,6-diisopropylphenylimino)ethyl]pyridine, 2[(1-(methylimino)ethyl]pyridine, 2[(1-(ethylimino)ethyl]pyridine, 2[(1-(isopropylimino)ethyl]pyridine, 2[(1-(tert-butylimino)ethyl]pyridine, diimines, for example 1,2-bis(methylimino)ethane, 1,2-bis(ethylimino)ethane, 1,2-bis(isopropylimino)ethane, 1,2-bis(tert-butylimino)ethane, 2,3-bis(methylimino)butane, 2,3-bis(ethylimino)butane, 2,3-bis(isopropylimino)butane, 2,3-bis(tert-butylimino)butane, 1,2-bis(phenylimino)ethane, 1,2-bis(2-methylphenylimino)ethane, 1,2-bis(2,6- diisopropylphenylimino)ethane, 1,2-bis(2,6-di-tert-butylphenylimino)ethane, 2,3-bis(phenylimino)butane, 2,3-bis(2-methylphenylimino)butane, 2,3-bis(2,6-di-isopropylphenylimino)butane, 2,3-bis(2,6-di-tert-butylphenylimino)butane, heterocycles containing two nitrogen atoms, for example 2,2'-bipyridine, o-phenanthroline, diphosphines, for example bisdiphenylphosphinomethane, bisdiphenylphosphinoethane, bis(diphenylphosphino)propane, such as bis(dimethylphosphino)methane, such as bis(dimethylphosphino)ethane, bis(dimethylphosphino)propane, such as bis(diethylphosphino)methane, bis(diethylphosphino)ethane, bis(diethylphosphino)propane, bis(di-tert-butylphosphino)methane, such as bis(di-tert-butylphosphino)ethane, bis(tert-butylphosphino)propane, 1,3-diketonates derived from 1,3-diketones, for example acetylacetone, benzoylacetone, 1,5-diphenylacetylacetone, dibenzoylmethane, bis(1,1,1-tri-fluoroacetyl)methane, 3-ketonates derived from 3-ketoesters, for example ethyl acetoacetate, carboxylates derived from aminocarboxylic acids, for example pyridine-2-carboxylic acid, quinoline-2-carboxylic acid, glycine, dimethylglycine, alanine, dimethylaminoalanine, salicyliminates derived from salicylimines, for example methylsalicylimine, ethylsalicylimine, phenylsalicylimine, dialkoxides derived from dialcohols, for example ethylene glycol, 1,3-propylene glycol, dithiolates derived from dithiols, for example 1,2-ethylenedithiol, 1,3-propylenedithiol.

The present invention further provides processes for preparing the compounds (1) to (32) by reacting the compounds (33) to (64) according to scheme 5:

Scheme 5:

Compounds (33)

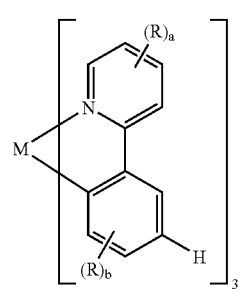

Compounds (34)

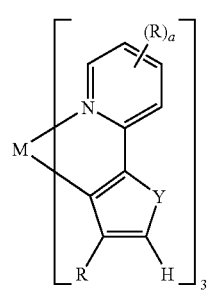

Compounds (35)

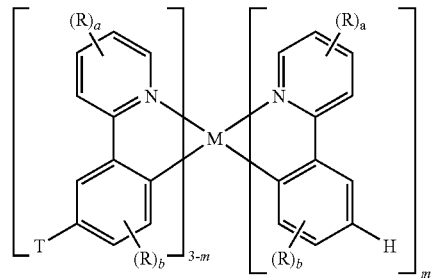

Compounds (36)

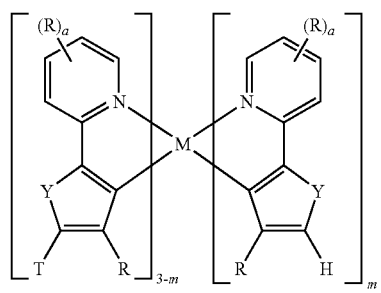

Compounds (37)

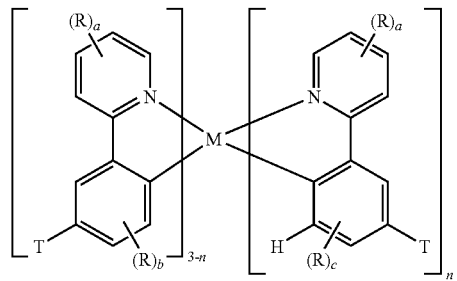

Compounds (38)

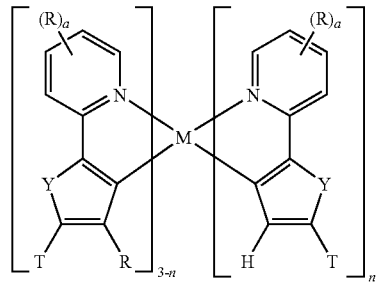

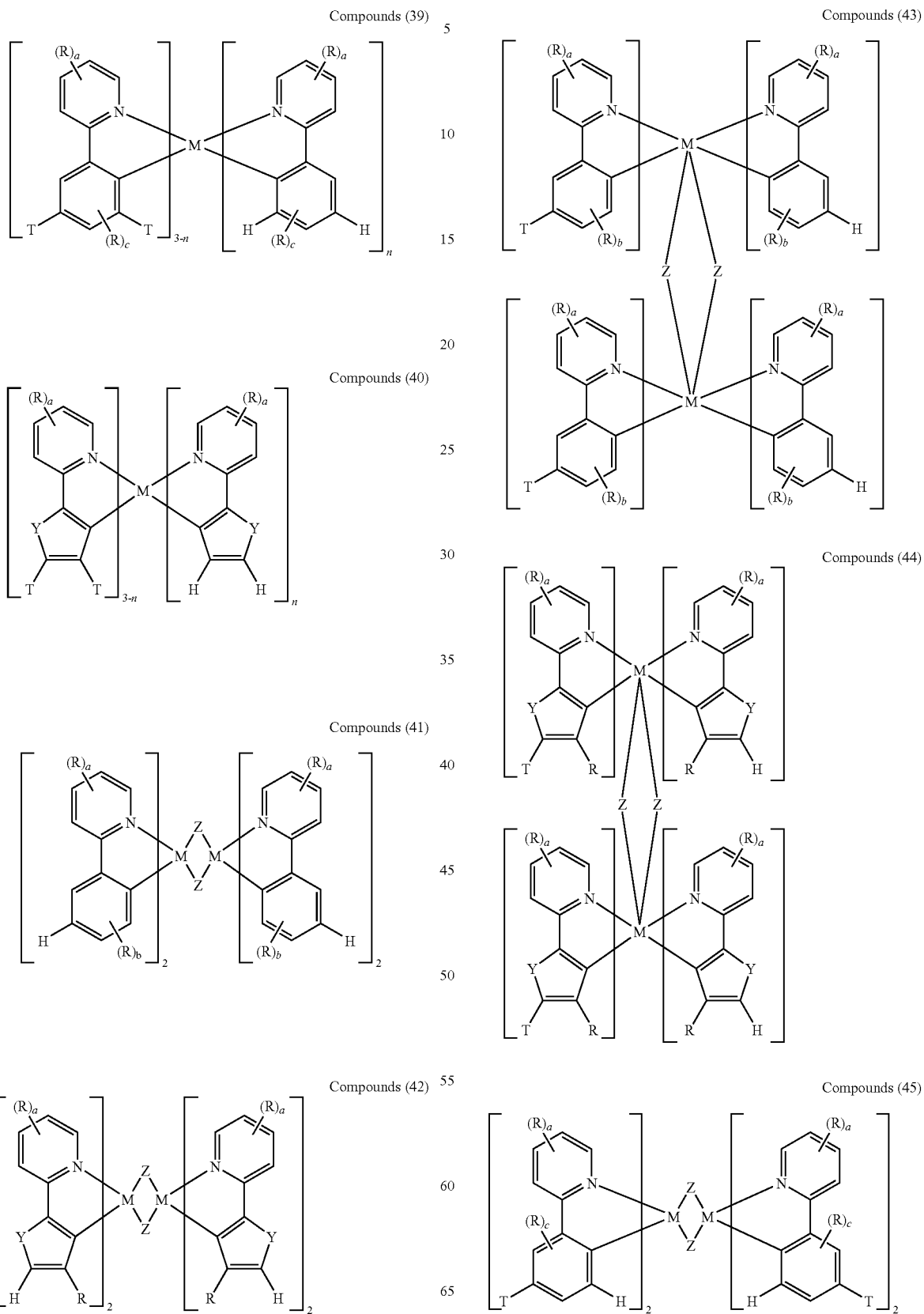

Compounds (46)
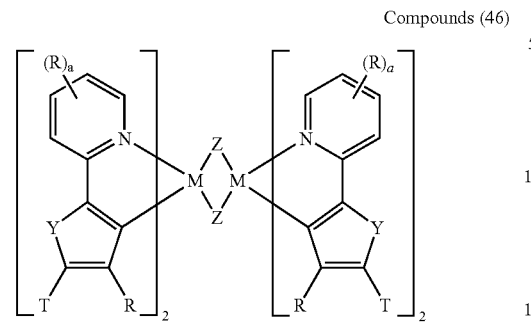
Compounds (47)
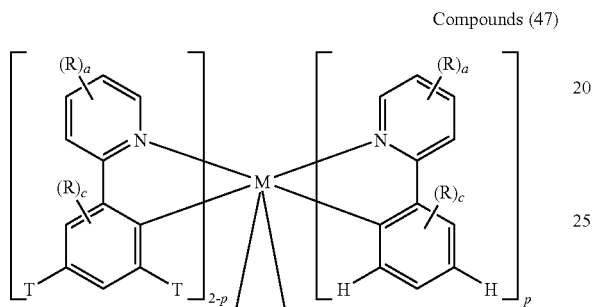
Compounds (48)
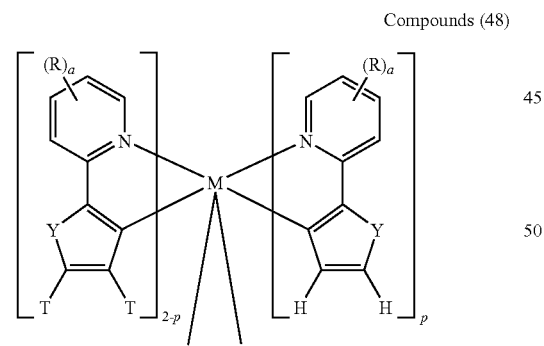
Compounds (49)
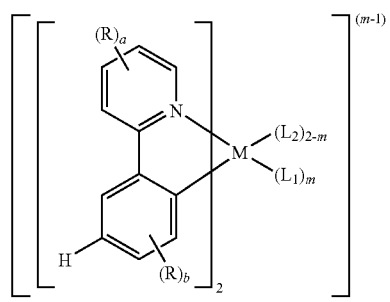
Compounds (50)
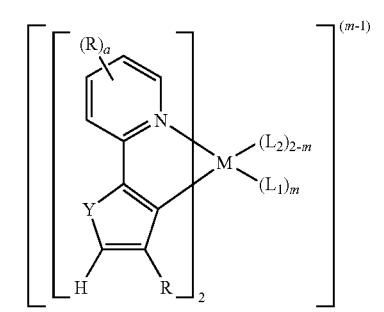
Compounds (51)
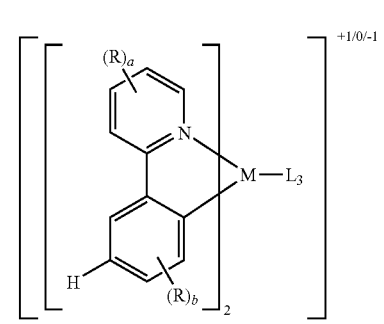
Compounds (52)
Compounds (53)

Compounds (54)
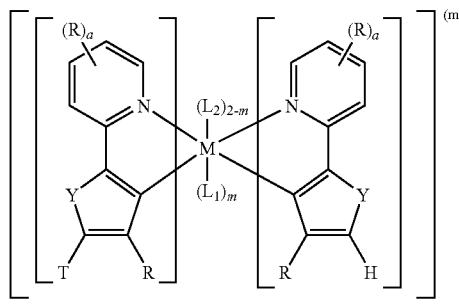
Compounds (55)
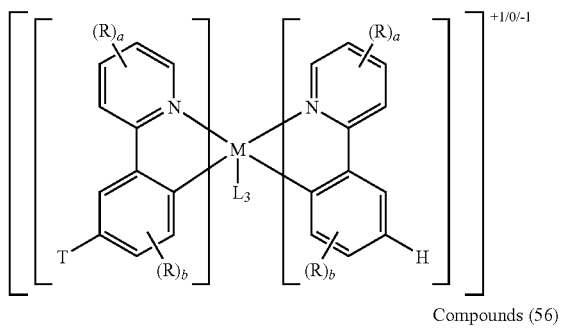
Compounds (56)
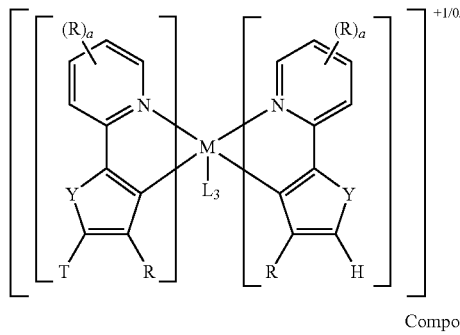
Compounds (57)
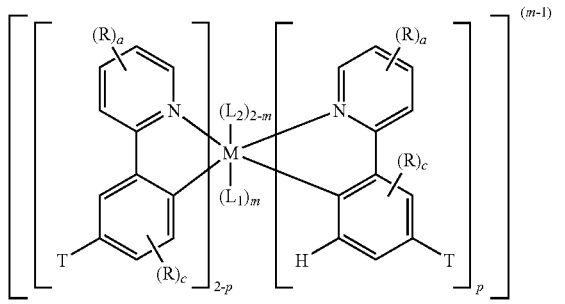
Compounds (58)
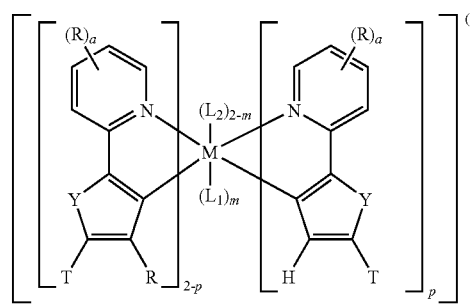
Compounds (59)
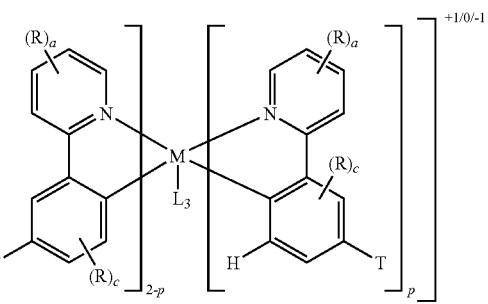
Compounds (60)
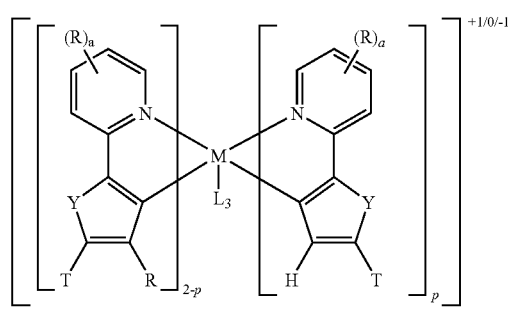
Compounds (61)
Compounds (62)
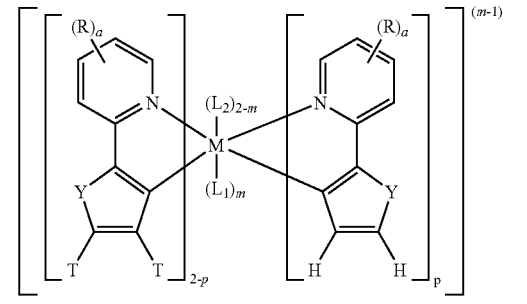
Compounds (63)
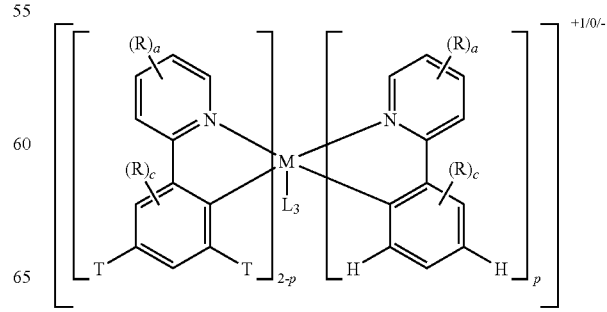

-continued

Compounds (64)

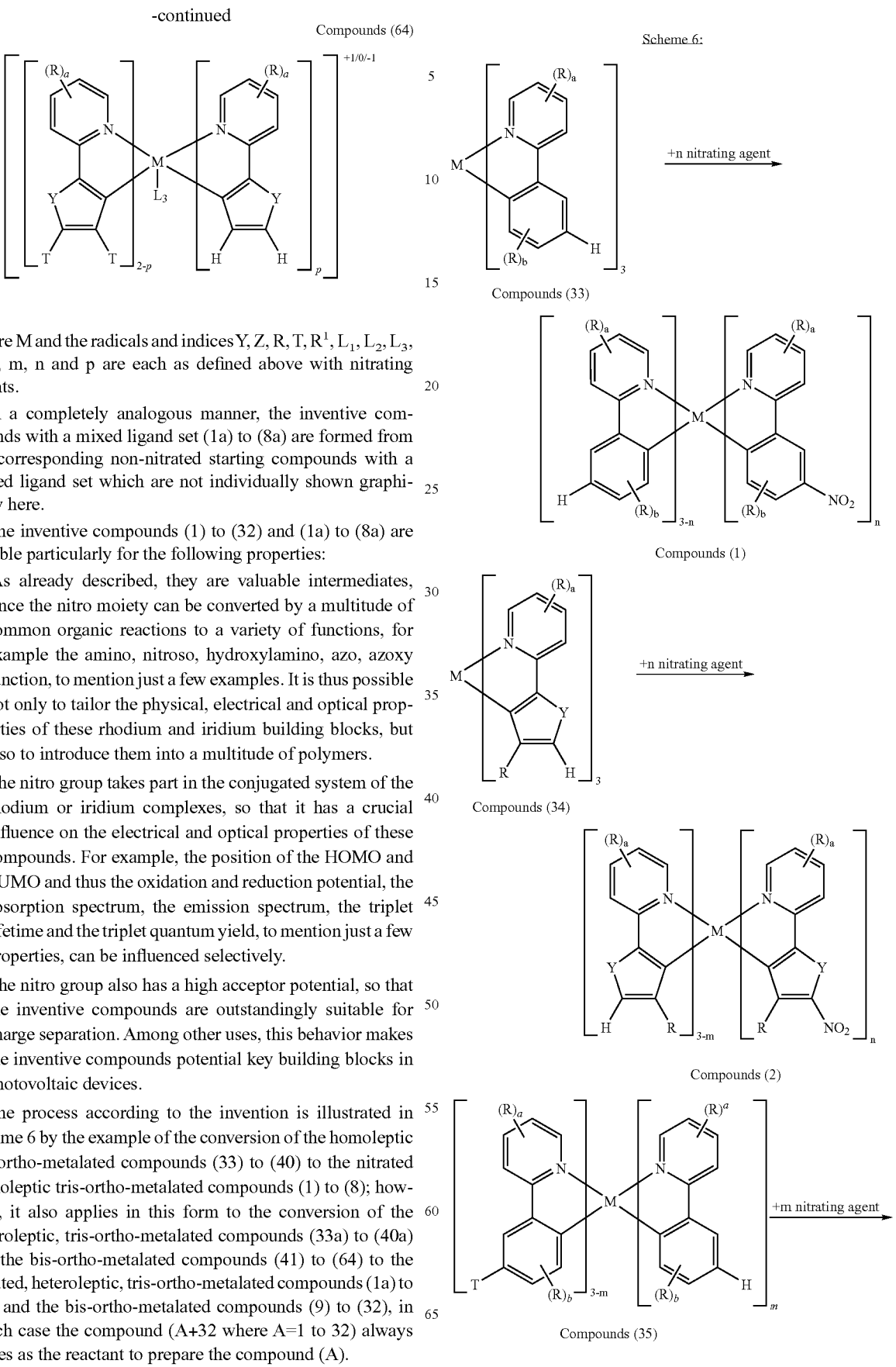

where M and the radicals and indices Y, Z, R, T, $R^1$, $L_1$, $L_2$, $L_3$, a, b, m, n and p are each as defined above with nitrating agents.

In a completely analogous manner, the inventive compounds with a mixed ligand set (1a) to (8a) are formed from the corresponding non-nitrated starting compounds with a mixed ligand set which are not individually shown graphically here.

The inventive compounds (1) to (32) and (1a) to (8a) are notable particularly for the following properties:

1) As already described, they are valuable intermediates, since the nitro moiety can be converted by a multitude of common organic reactions to a variety of functions, for example the amino, nitroso, hydroxylamino, azo, azoxy function, to mention just a few examples. It is thus possible not only to tailor the physical, electrical and optical properties of these rhodium and iridium building blocks, but also to introduce them into a multitude of polymers.

2) The nitro group takes part in the conjugated system of the rhodium or iridium complexes, so that it has a crucial influence on the electrical and optical properties of these compounds. For example, the position of the HOMO and LUMO and thus the oxidation and reduction potential, the absorption spectrum, the emission spectrum, the triplet lifetime and the triplet quantum yield, to mention just a few properties, can be influenced selectively.

3) The nitro group also has a high acceptor potential, so that the inventive compounds are outstandingly suitable for charge separation. Among other uses, this behavior makes the inventive compounds potential key building blocks in photovoltaic devices.

The process according to the invention is illustrated in scheme 6 by the example of the conversion of the homoleptic tris-ortho-metalated compounds (33) to (40) to the nitrated homoleptic tris-ortho-metalated compounds (1) to (8); however, it also applies in this form to the conversion of the heteroleptic, tris-ortho-metalated compounds (33a) to (40a) and the bis-ortho-metalated compounds (41) to (64) to the nitrated, heteroleptic, tris-ortho-metalated compounds (1a) to (8a) and the bis-ortho-metalated compounds (9) to (32), in which case the compound (A+32 where A=1 to 32) always serves as the reactant to prepare the compound (A).

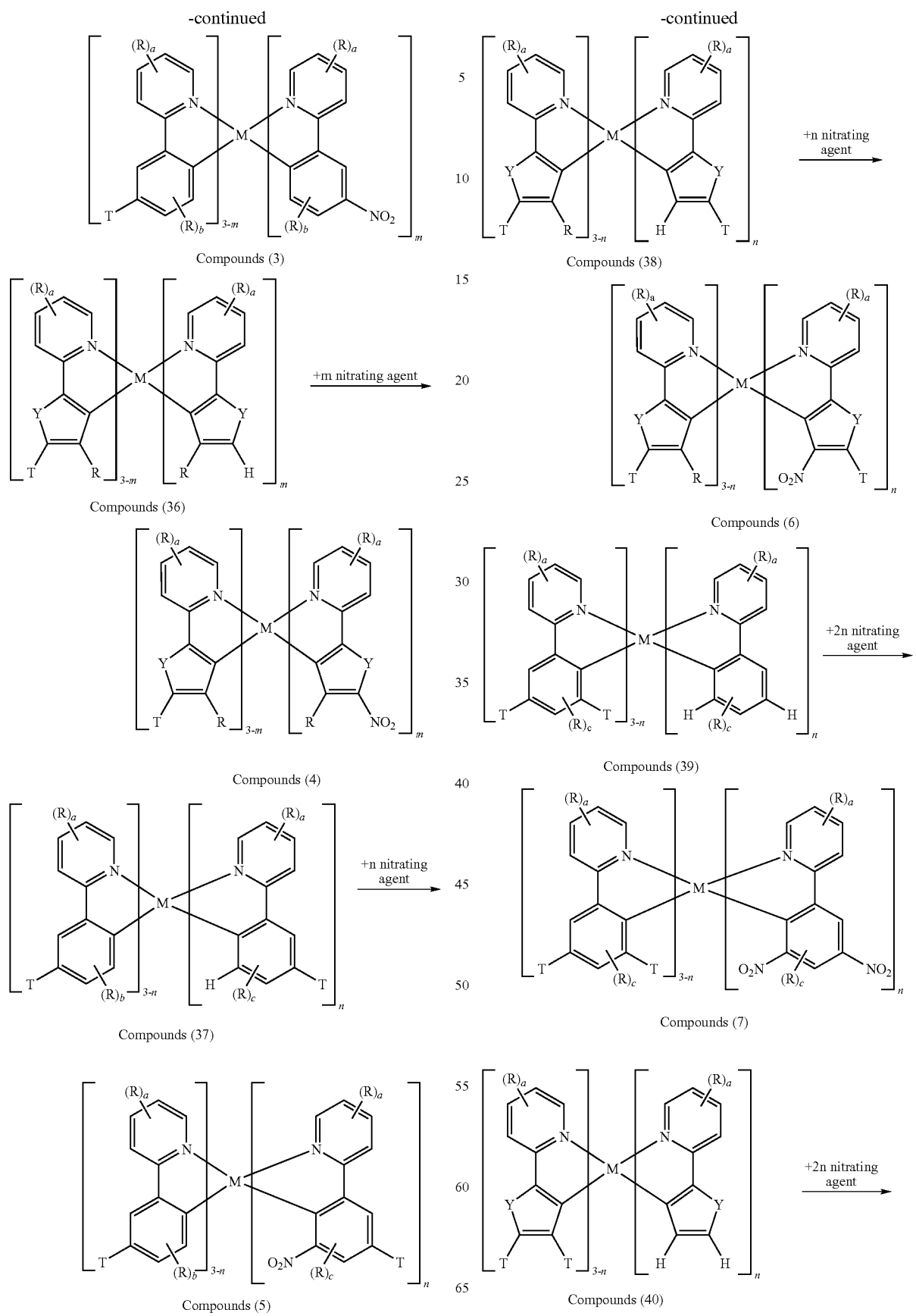

-continued

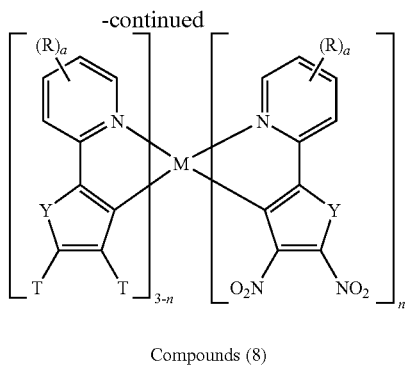

Compounds (8)

Inventive nitrating agents are nitric acid, optionally in combination with a further acid, for example sulfuric acid or phosphoric acid, dinitrogen tetroxide, dinitrogen pentoxide, nitronium salts of the $NO_2A$ type, where A is a suitable inert anion such as $BF_4^-$, $PF_6^-$, $SbF_6^-$ or $CF_3SO_3^-$, alkali metal or alkaline earth metal nitrates such as lithium nitrate, sodium nitrate, potassium nitrate, magnesium nitrate, optionally in the presence of an acid such as sulfuric acid, phosphoric acid, acetic acid, propionic acid or trifluoroacetic acid or mixtures thereof, and/or of a carboxylic anhydride such as acetic anhydride or propionic anhydride, transition metal nitrates such as iron(II) nitrite or nitrate, iron(III) nitrite or nitrate, cobalt(II) nitrite or nitrate, cobalt(III) nitrite or nitrate, nickel(II) nitrite or nitrate, or copper(II) nitrite or nitrate, optionally in the presence of an acid such as sulfuric acid, phosphoric acid, acetic acid, propionic acid or trifluoroacetic acid, and/or of a carboxylic anhydride such as acetic anhydride or propionic anhydride or mixtures thereof.

The inventive nitrating agents may be divided into those which lead to a selective nitration of the para-positions (corresponding to the 5' position in scheme 7) and those which lead to a pernitration of the ortho- and para-positions (corresponding to the 3' and 5' positions in phenylpyridine ligands and the 4' and 5' positions in the thiophenylpyridines in scheme 7). The former group includes dilute nitric acid and nitronium salts used in stoichiometric amounts, or else the alkali metal and alkaline earth metal nitrates in organocarboxylic acids and the anhydrides thereof, especially at temperatures lower than or equal to room temperature.

The latter group includes concentrated nitric acid, optionally in combination with a further acid, nitronium salts and also the alkali metal and alkaline earth metal nitrates in organocarboxylic acids and the anhydrides thereof, when they are used in superstoichiometric amounts and at temperatures above room temperature.

In the process according to the invention, a stoichiometric ratio of the nitrating agents, based on the content of active $NO_2^+$ or of the corresponding nitrating species, to the compounds (33) or (34) of 1:1 leads selectively to the compounds (1) or (2) where n=1. This is a surprising and unforeseeable result.

In the process according to the invention, a stoichiometric ratio of the nitrating agents, based on the content of active $NO_2^+$ or of the corresponding nitrating species, to the compounds (33) or (34) of 2:1 leads selectively to the compounds (1) or (2) where n=2. This is a surprising and unforeseeable result.

In the process according to the invention, a stoichiometric ratio of the nitrating agents which lead to exclusive para-nitration, based on the content of active $NO_2^+$ or of the corresponding nitrating species, to the compounds (33) or (34) of from 3:1 to 1000:1 leads selectively to the compounds (1) or (2) where n=3. This is a surprising and unforeseeable result.

In the process according to the invention, a stoichiometric ratio of the nitrating agents, based on the content of active $NO_2^+$ or of the corresponding nitrating species, to the compounds (35) or (36) of 1:1 leads selectively to the compounds (3) or (4) where m=1. This is a surprising and unforeseeable result.

In the process according to the invention, a stoichiometric ratio of the nitrating agents, based on the content of active $NO_2^+$ or of the corresponding nitrating species, to the compounds (35) or (36) of from 2:1 to 1000:1 leads selectively to the compounds (3) or (4) where m=2. This is a surprising and unforeseeable result.

In the process according to the invention, a stoichiometric ratio of the nitrating agents, based on the content of active $NO_2^+$ or of the corresponding nitrating species, to the compounds (37) or (38) of 1:1 leads selectively to the compounds (5) or (6) where n=1. This is a surprising and unforeseeable result.

In the process according to the invention, a stoichiometric ratio of the nitrating agents, based on the content of active $NO_2^+$ or of the corresponding nitrating species, to the compounds (37) or (38) of 2:1 leads selectively to the compounds (5) or (6) where n=2. This is a surprising and unforeseeable result.

In the process according to the invention, a stoichiometric ratio of the nitrating agents, based on the content of active $NO_2^+$ or of the corresponding nitrating species, to the compounds (37) or (38) of from 3:1 to 1000:1 leads selectively to the compounds (5) or (6) where n=3. This is a surprising and unforeseeable result.

In the process according to the invention, a stoichiometric ratio of the nitrating agents which lead to ortho- and para-nitration, based on the content of active $NO_2^+$ or of the corresponding nitrating species, to the compounds (39) or (40) of 2:1 leads selectively to the compounds (7) or (8) where n=1. This is a surprising and unforeseeable result.

In the process according to the invention, a stoichiometric ratio of the nitrating agents which lead to ortho- and para-nitration, based on the content of active $NO_2^+$ or of the corresponding nitrating species, to the compounds (39) or (40) of 4:1 leads selectively to the compounds (7) or (8) where n=2. This is a surprising and unforeseeable result.

In the process according to the invention, a stoichiometric ratio of the nitrating agents which lead to ortho- and para-nitration, based on the content of active $NO_2^+$ or of the corresponding nitrating species, to the compounds (39) or (40) of from 6:1 to 1000:1 leads selectively to the compounds (7) or (8) where n=3. This is a surprising and unforeseeable result.

The stoichiometric ratios described above for the homoleptic, tris-ortho-metalated compounds apply analogously also to the heteroleptic, bis- and tris-ortho-metalated compounds and are apparent to those skilled in the art without any further inventive activity. For this reason, an explanation is dispensed with at this point.

Moreover, the stoichiometric ratios described here are preferred embodiments of the present invention, since they lead to uniformly substituted products. It goes without saying that slight deviations from the abovementioned ratios still lead to good to acceptable results.

Inventive reaction media are protic or aprotic, halogen-free or halogenated solvents, for example carboxylic acids such as acetic acid or propionic acid, carboxylic anhydrides such as acetic anhydride or propionic anhydride, nitrites such as acetonitrile, propionitrile or benzonitrile, ethers such as diethyl ether, THF or dioxane, aromatic hydrocarbons which are deactivated with respect to the nitration, such as benzonitrile, nitrobenzene or chlorobenzene, sulfones such as dimethylsulfone or sulfolane, halogenated hydrocarbons such as dichloromethane, trichloromethane, 1,1-dichloroethane, 1,2-dichloroethane, 1,1,2,2-tetrachloroethane.

According to the invention, the reaction is carried out within the temperature range of from −78° C. to 150° C., preferably at from −30° C. to 100° C., very preferably at from 0° C. to 60° C.

According to the invention, the concentration of the rhodium-containing or iridium-containing reactants, compounds (33) to (64), is in the range from 0.0005 mol/l to 2 mol/l, more preferably in the range from 0.002 mol/l to 0.1 mol/l.

According to the invention, the rhodium-containing or iridium-containing reactants may be present dissolved or suspended in the reaction medium.

According to the invention, the reaction is carried out within from 10 minutes up to 100 hours, preferably within from 1 h to 40 h.

It is possible by the synthetic methods illustrated here to prepare compounds including the examples of compounds (1) to (32) shown below.

Example 1

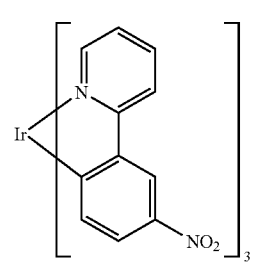

Example 2

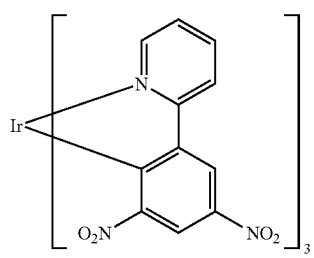

Example 3

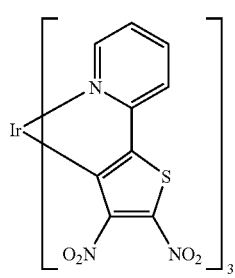

Example 4

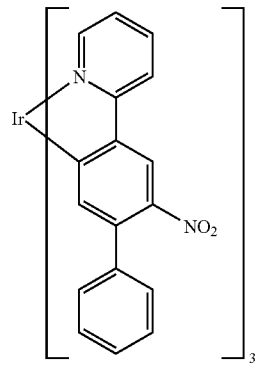

Example 5

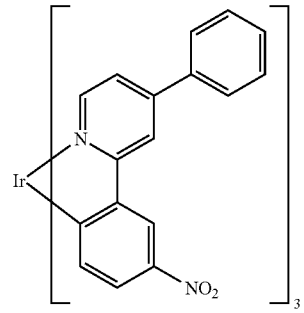

Example 6

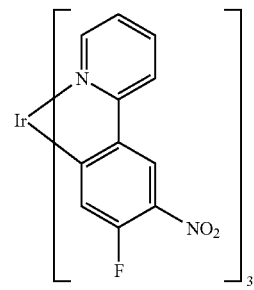

Example 7

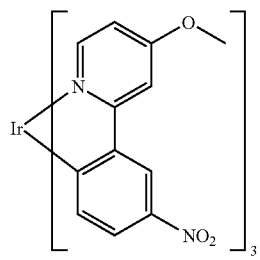

Example 8

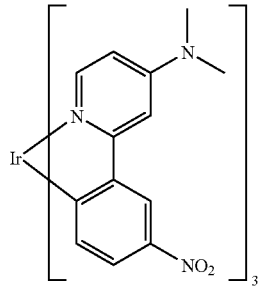

-continued
Example 9
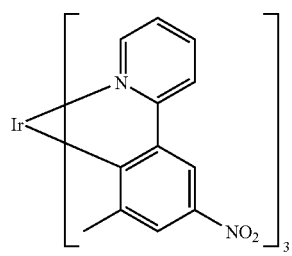
Example 10
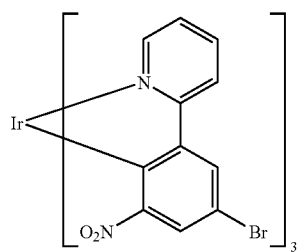
Example 11
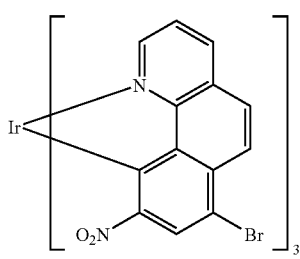
Example 12
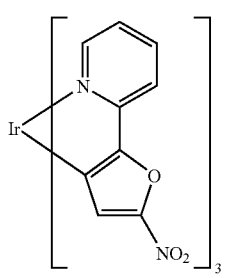
Example 13
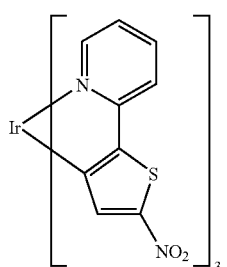
Example 14
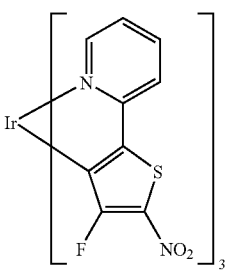
-continued
Example 15
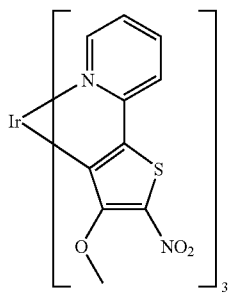
Example 16
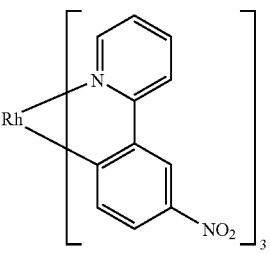
Example 17
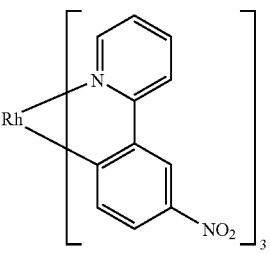
Example 18
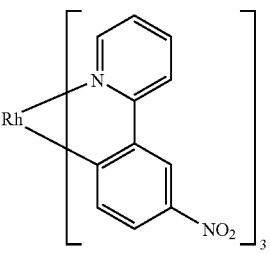
Example 19
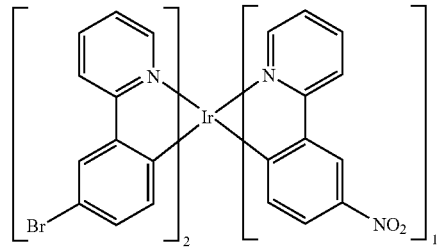
Example 20
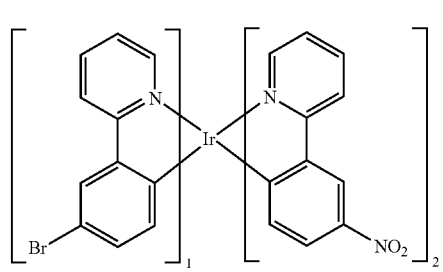

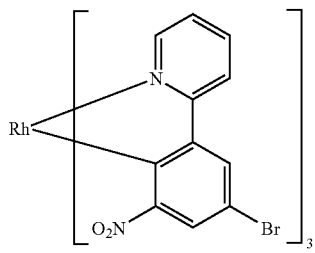
Example 21
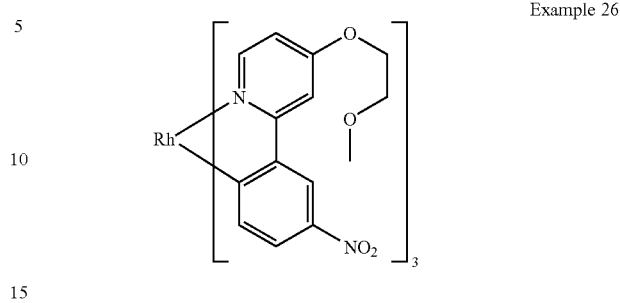
Example 26
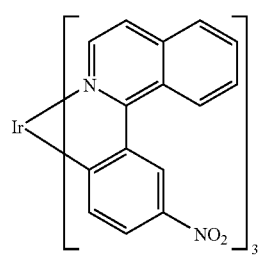
Example 22
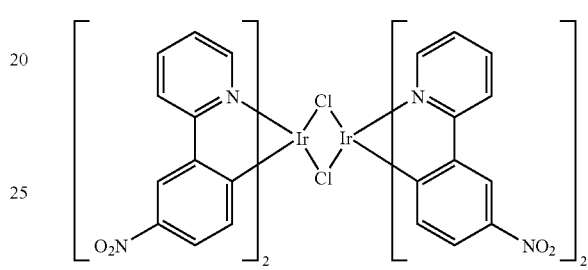
Example 27
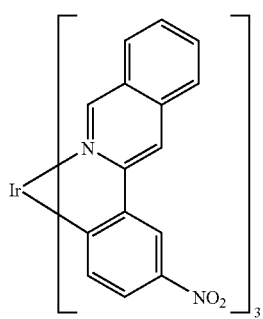
Example 23
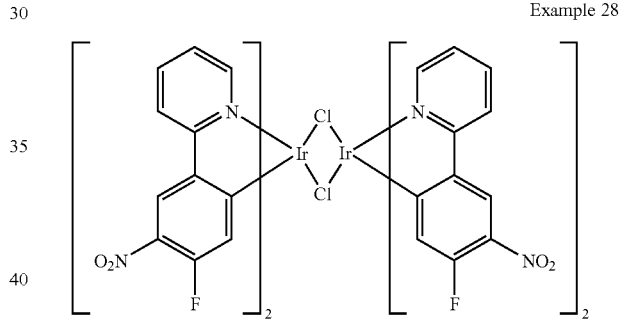
Example 28
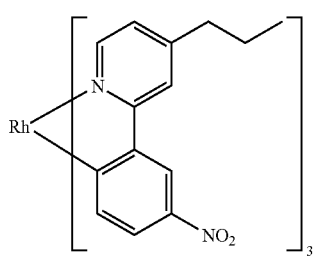
Example 24
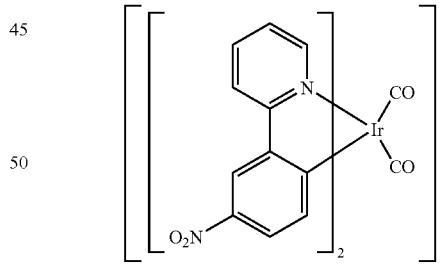
Example 29
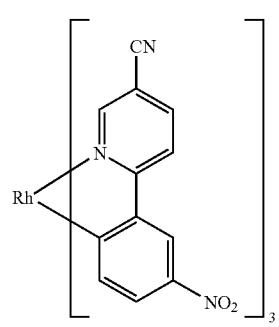
Example 25
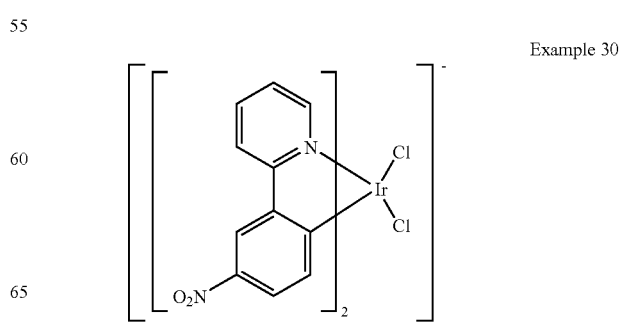
Example 30

Example 31

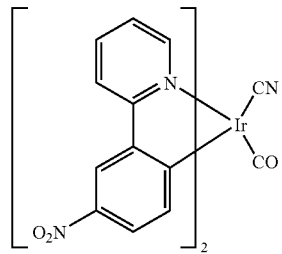

Example 33

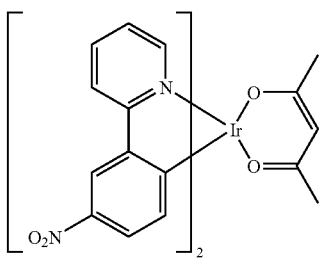

Example 34

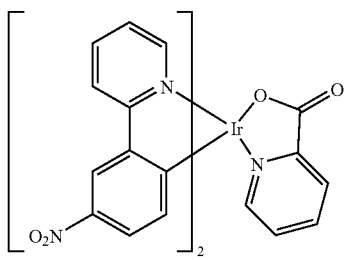

Example 35

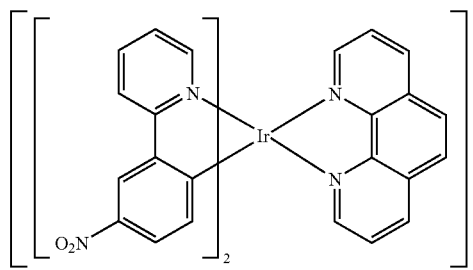

The thus obtained inventive compounds may, if appropriate after further functionalization, find use, for example, as comonomers for obtaining corresponding conjugated or else semiconjugated or nonconjugated polymers. For instance, they may be polymerized into polymers which are soluble in organic solvents including polyfluorenes (for example according to EP-A-842208 or WO 00/22026), poly-spiro-bifluorenes (for example according to EP-894107), poly-para-phenylenes (for example according to WO 92/18552), polycarbazoles or else polythiophenes (for example according to EP-A-1028136), in which case they may occur either in the polymer chain itself or as an end group on the chain ends, or if appropriate in side chains of the polymer. The inventive compounds are bonded within the polymer as shown in formula (3'), (4'), (5'), (6'), (7') and/or (8'):

Compounds (3')

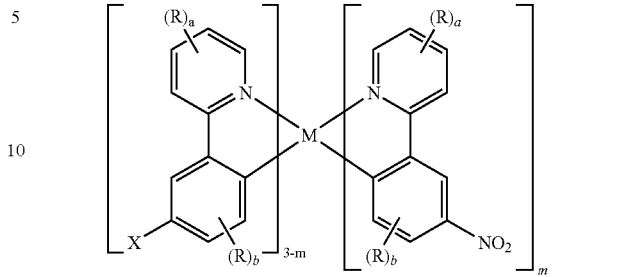

Compounds (4')

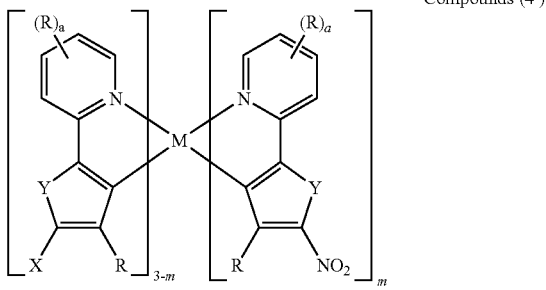

Compounds (5')

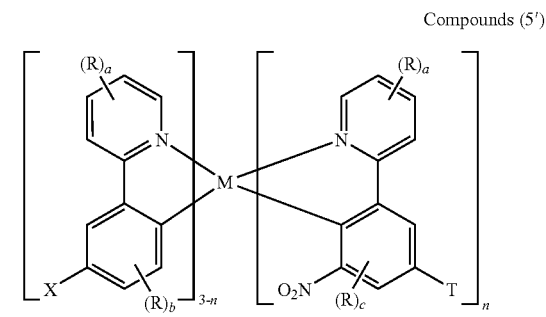

Compounds (6')

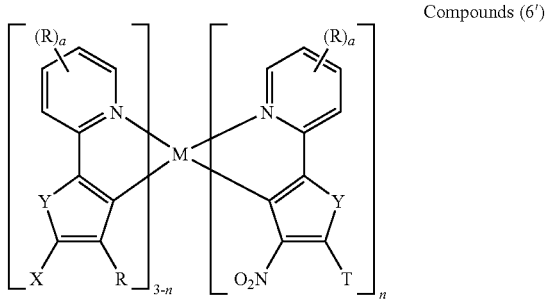

Compounds (7')

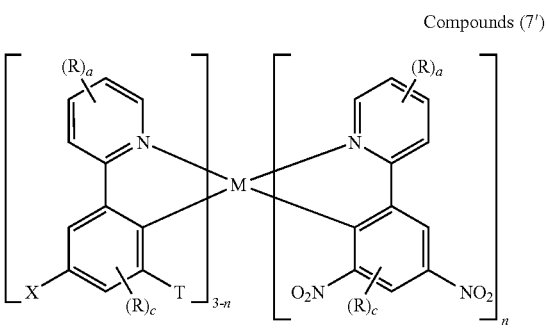

Compounds (8')

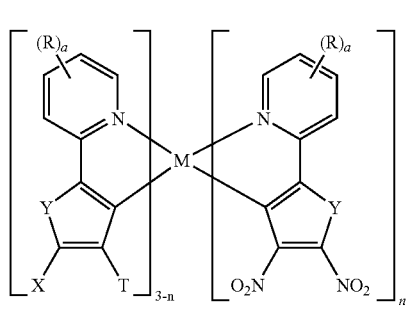

and/or as shown in the formulae (3a'), (4a'), (5a'), (6a'), (7a') and/or (8a'):

Compounds (3a')

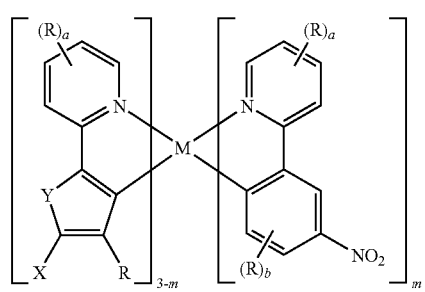

Compounds (4a')

Compounds (5a')

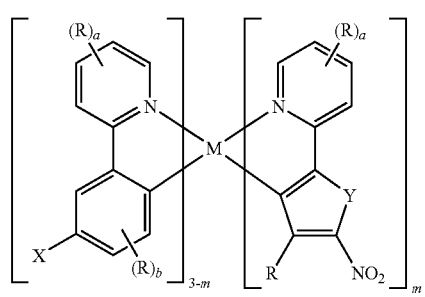

Compounds (6a')

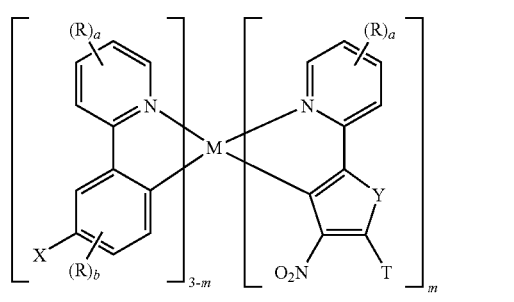

Compounds (7a')

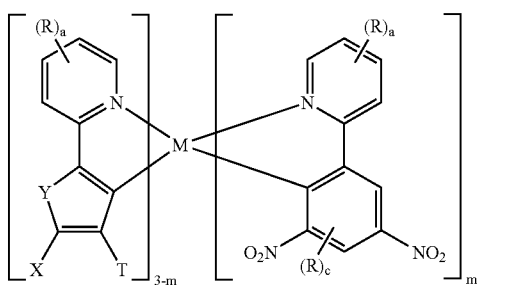

Compounds (8a')

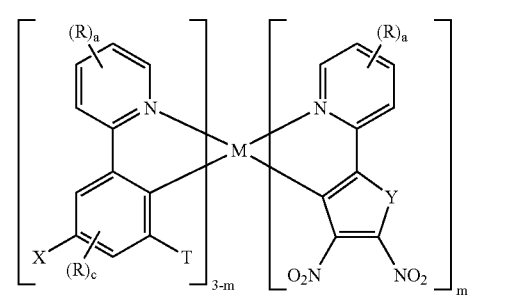

where X is a bond to the conjugated, semiconjugated or nonconjugated polymer, and the further symbols and indices are each as defined above for compound (3) to (8) or (3a) to (8a).

In addition, the inventive compounds may also be bonded within the polymer as shown in formula (17'), (18'), (19'), (20'), (21'), (22'), (23'), (24'), (25'), (26'), (27'), (28'), (29'), (30'), (31') and/or (32'):

Compounds (17')

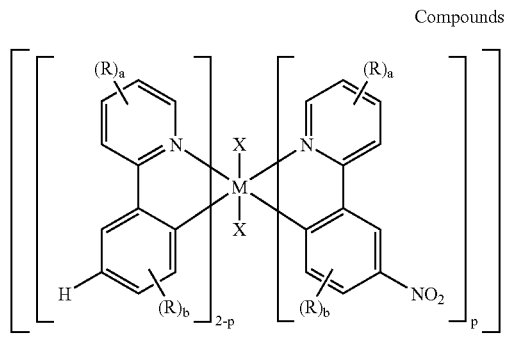

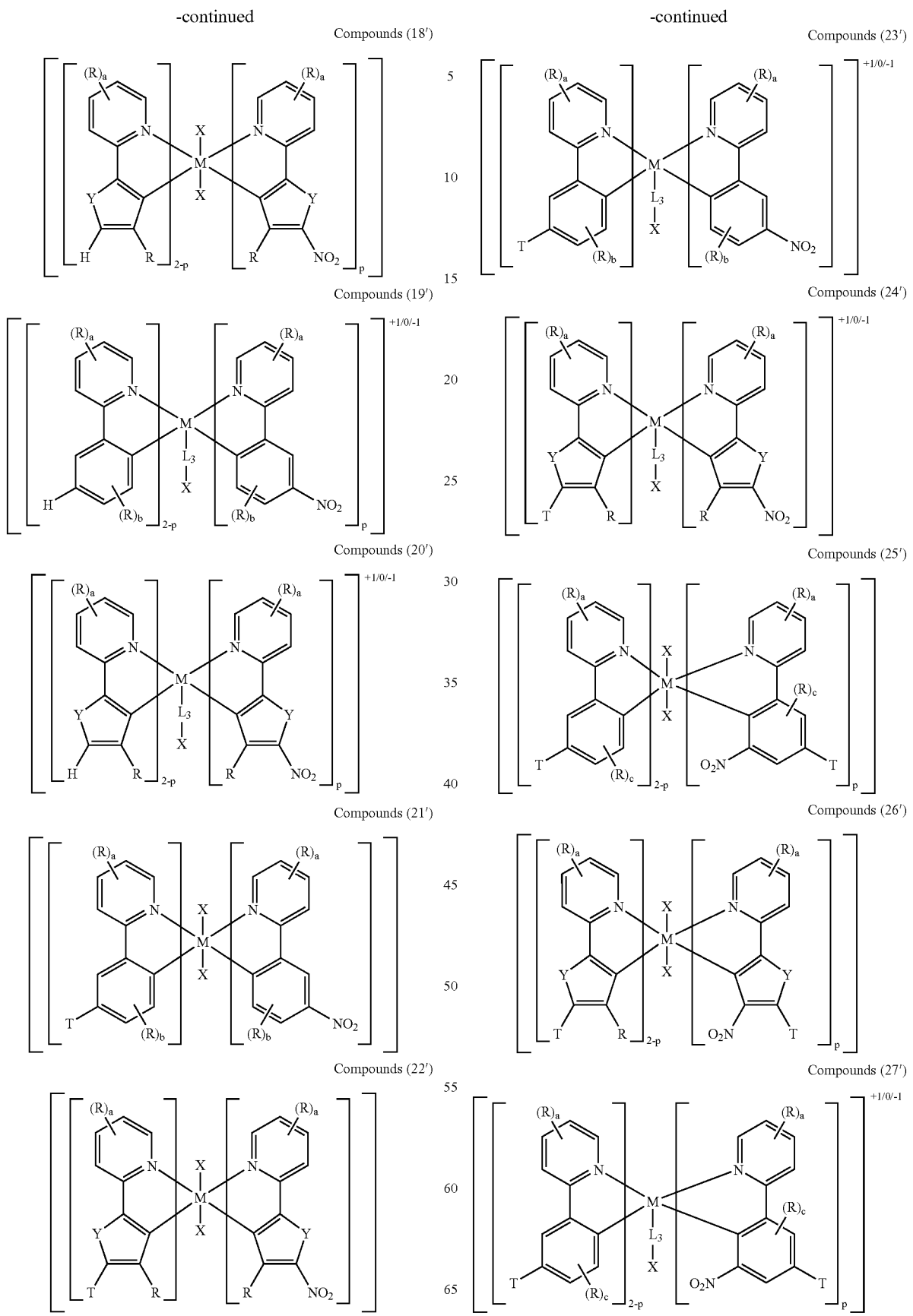

Compounds (28′)

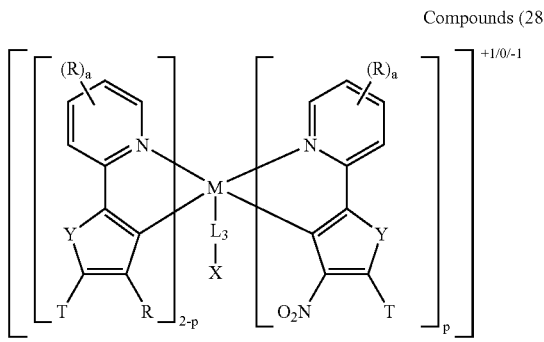

Compounds (29′)

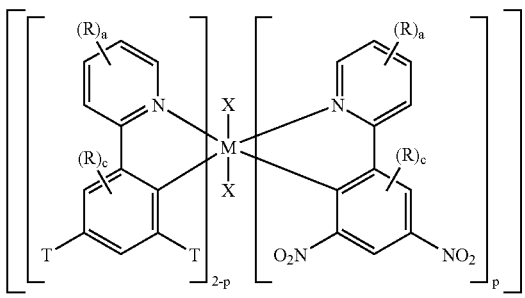

Compounds (30′)

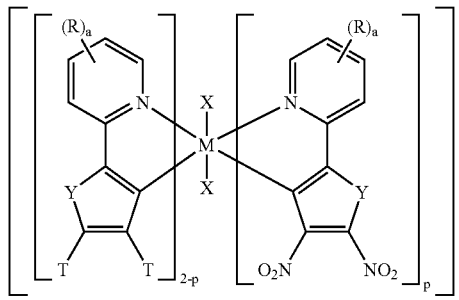

Compounds (31′)

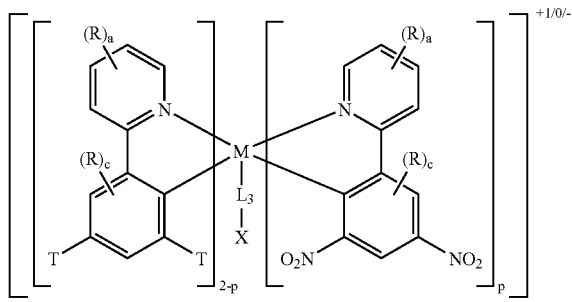

Compounds (32′)

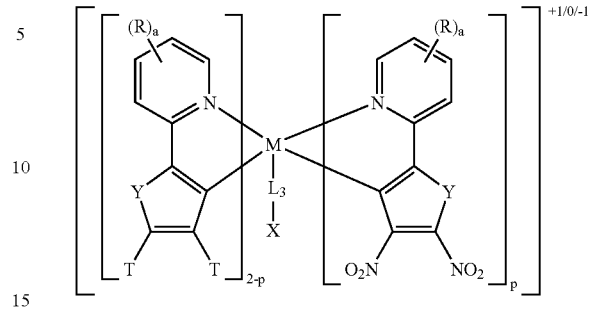

where X is a bond to the conjugated, semiconjugated or nonconjugated polymer and the further symbols and indices are each as defined above for compound (17) to (32).

The inventive polymers are notable for their good solubility of at least 0.1% by weight in organic aprotic solvents such as aromatic hydrocarbons, for example toluene, xylene, anisole, chlorobenzene, naphthalene, methylnaphthalene, tetralin, such as ethers, for example tetrahydrofuran and dioxane, such as halogenated hydrocarbons, for example dichloromethane, chloroform, 1,2-dichloroethane, 1,1,2,2-tetrachloroethane, such as carboxamides, for example dimethylformamide, dimethylacetamide and N-methylpyrrolidone.

The polyfluorenes disclosed in EP-A-842208 and WO 00/22026 form part of this description.

The poly-spiro-bifluorenes disclosed in EP-894107 form part of this description.

The poly-para-phenylenes disclosed in WO 92/18552 form part of this description.

The polythiophenes disclosed in EP-A-1028136 form part of this description.

The inventive nitro-substituted metal complexes and the inventive polymers which contain inventive nitro-substituted metal complexes find use as active components in electronic components, for example organic light-emitting diodes (OLEDs), organic integrated circuits (O-ICs), organic field-effect transistors (O-FETs), organic thin-film transistors (O-TFTs), organic solar cells (O-SCs) or else organic laser diodes (O-lasers).

The invention therefore also provides electronic components, for example organic or polymeric light-emitting diodes (OLEDs or PLEDs), organic integrated circuits (O-ICs), organic field-effect transistors (O-FETs), organic thin-film transistors (O-TFTs), organic solar cells (O-SCs) or organic laser diodes (O-lasers), comprising one or more inventive nitro-substituted metal complexes or one or more inventive polymers which contain one or more inventive nitro-substituted metal complexes.

The inventive compounds may of course also be functionalized further by common organic reaction types, and thus converted to extended low molecular weight Rh or Ir complexes. An example to be mentioned here is the reduction of the nitro groups to amino, nitroso, hydroxylamino, azo and azoxy functions.

The present invention is illustrated in detail by the examples which follow without any intention to restrict it thereto. Those skilled in the art can prepare further inventive complexes or apply the process according to the invention from the descriptions without any inventive activity.

EXAMPLES

Synthesis of Symmetrically and Asymmetrically Functionalized Tris-Ortho-Metalated Organorhodium or Organoiridium Compounds:

Unless stated otherwise, the syntheses below were carried out under air using commercial solvents. The reactants were purchased from ALDRICH. fac-Tris[2-(2-pyridinyl-κN)phenyl-κC]-iridium(III) was prepared as described in the published application WO 02/060910.

Numbering scheme for the assignment of the $^1$H NMR signals [according to: C. Coudret, S. Fraysse, J.-P-Launay, Chem. Commun., 1998, 663-664]:

Scheme 7:

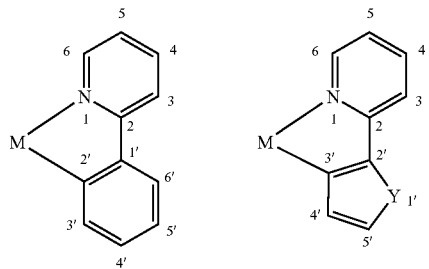

Example 1 fac-Tris[2-(2-pyridinyl-κN)(5-nitrophenyl)-κC]iridium(III)

2.08 g of fuming nitric acid, 100%, P.A. (Merck) were diluted with 0.2 ml of water. This mixture was added to an efficiently stirred solution, cooled to 0° C., of 6.548 g (10.0 mmol) of fac-Tris[2-(2-pyridinyl-κN)phenyl-κC]iridium (III) in 1500 ml of dichloromethane. The reaction mixture was stirred at 0° C. for a further 3 h. After 200 ml of saturated sodium carbonate solution had been added, the aqueous phase was removed, and the organic phase was washed twice with 100 ml each time of water, concentrated to 300 ml and then admixed with 500 ml of ethanol. Subsequently, the microcrystalline precipitate was filtered off (P4), washed three times with 50 ml of ethanol, recrystallized from DMSO/ethanol and then dried under reduced pressure (60° C., 10$^{-4}$ mbar). The yield, at a purity of >99.5% by $^1$H NMR, was 6.693 g-6.814 g, corresponding to 85.0%-86.6%.

$^1$H NMR (DMSO-d$_6$): [ppm]=8.34 (br. dd, 3H, $^3$J$_{HH}$=8.4 Hz, $^4$J$_{HH}$=1.2 Hz, H6), 8.03 (d, 3H, $^4$J$_{HH}$=2.0 Hz, H6'), 7.95 (ddd, 3H, $^3$J$_{HH}$=8.4 Hz, $^3$J$_{HH}$=8.4 Hz, $^4$J$_{HH}$=1.6 Hz, H5), 7.69 (dd, 3H, $^3$J$_{HH}$=5.4 Hz, $^4$J$_{HH}$=1.6 Hz, H3), 7.28 (ddd, 3H, $^3$J$_{HH}$=8.4 Hz, $^3$J$_{HH}$=5.4 Hz, $^4$J$_{HH}$=1.2 Hz, H4), 6.99 (dd, 3H, $^3$J$_{HH}$=8.1 Hz, $^4$J$_{HH}$=2.0 Hz, H4'), 6.73 (d, 3H, $^3$J$_{HH}$=8.1 Hz, H3').

Example 2 fac-Tris[2-(2-pyridinyl-κN)(3,5-dinitrophenyl)-κC]iridium(III)

6.27 g of fuming nitric acid, 100%, P.A. (Merck) were added at room temperature to an efficiently stirred solution of 6.548 g (10.0 mmol) of fac-Tris[2-(2-pyridinyl-κN)phenyl-κC]iridium(III) in 1500 ml of dichloromethane. The reaction mixture was stirred at 0° C. for a further 3 h. Subsequently, the microcrystalline precipitate was filtered off (P4), washed three times with 50 ml of ethanol/water (1:1 v:v) and washed three times with 50 ml of ethanol and then dried under reduced pressure (60° C., 10$^{-4}$ mbar). The yield, at a purity of >99.4% by $^1$H NMR, was 8.150 g-8.291 g, corresponding to 88.1%-89.6%.

$^1$H NMR (DMSO-d$_6$): [ppm]=8.83 (d, 31H, $^4$J$_{HH}$=2.3 Hz, H4' or H6'), 8.73 (m, 3H, H3 or H6), 8.11 (m, 3H, H4 or H5), 7.83 (d, 3H, $^4$J$_{HH}$=2.3 Hz, H6' or H4'), 7.35 (m, 3H, H5 or H4), 7.21 (m, 3H, H6 or H3).

Example 3 fac-Tris[2-(2-pyridinyl-κV)(3,5-dinitrophenyl)-κC]iridium(III)

12.378 g (66 mmol) of copper(II) nitrate were added to an efficiently stirred suspension, cooled to 0° C., of 6.548 g (10.0 mmol) of fac-Tris[2-(2-pyridinyl-κN)phenyl-κC]iridium (III) in 300 ml of acetic anhydride. The reaction mixture was warmed to room temperature and then stirred at 30° C. for a further 3 h. After 2000 ml of saturated sodium carbonate solution had been added, the microcrystalline precipitate was filtered off (P4). This was washed three times with 50 ml of ethanol. After the crude product had been recrystallized from DMSO/ethanol and dried under reduced pressure (60° C., 10$^{-4}$ mbar), the yield, at a purity of >99.6% by $^1$H NMR, was 8.341 g-8.702 g, corresponding to 90.1%-94.1%.

$^1$H NMR see Example 2.

What is claimed is:

1. Process for the preparation of the compounds of the formulae (1) to (32) and (1a) to (8a):

Compounds (1)

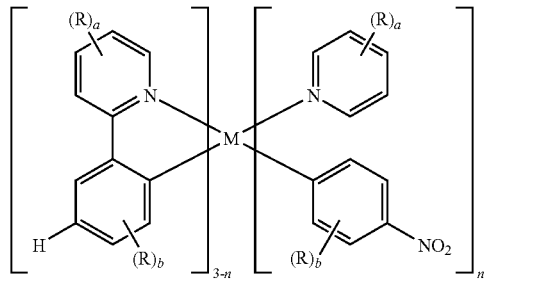

Compounds (2)

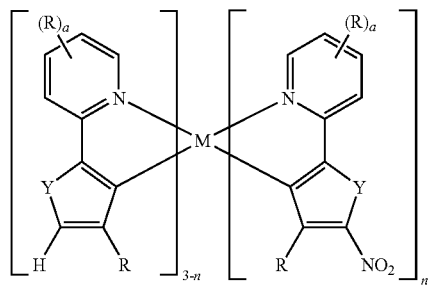

Compounds (3)
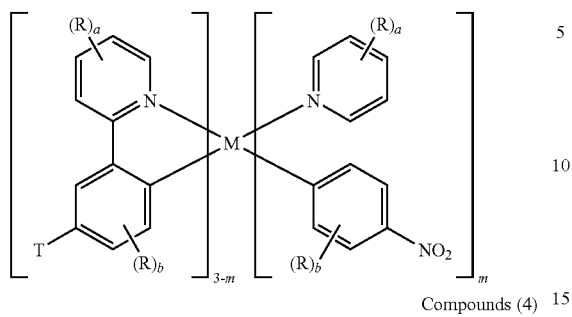
Compounds (4)
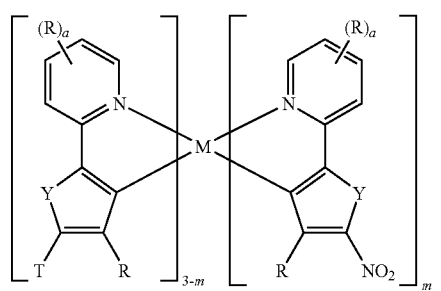
Compounds (5)
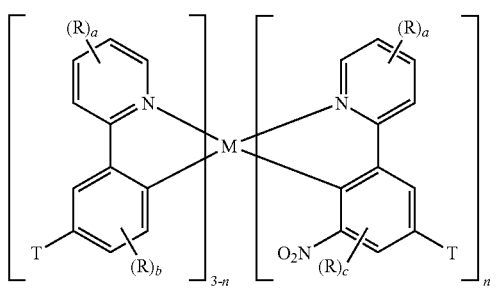
Compounds (6)
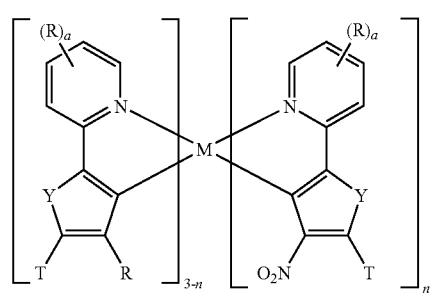
Compounds (7)
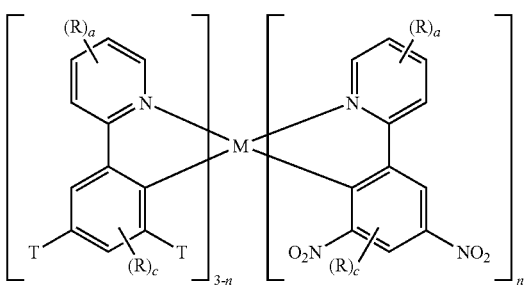
Compounds (8)
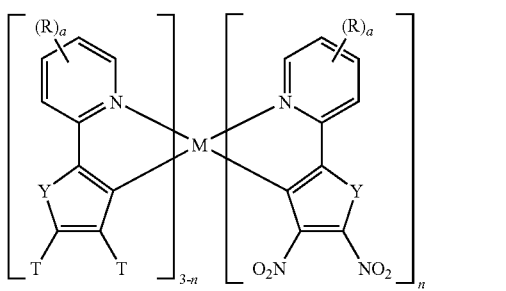
Compounds (1a)
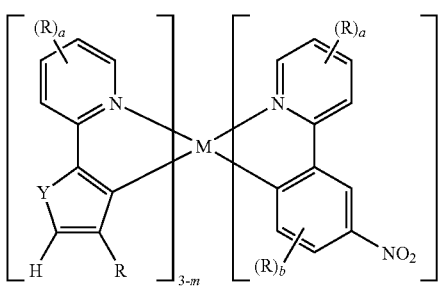
Compounds (2a)
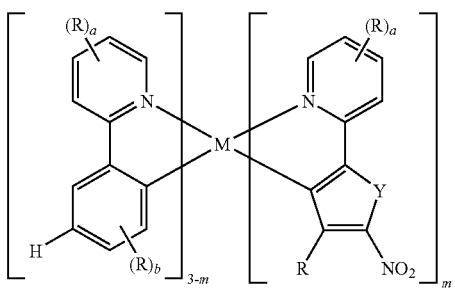
Compounds (3a)
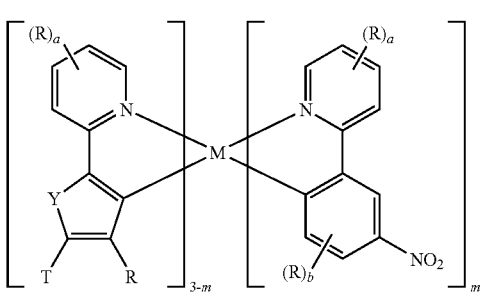
Compounds (4a)

-continued
Compounds (5a)
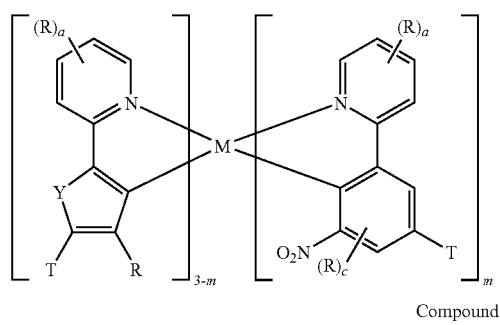
Compounds (6a)
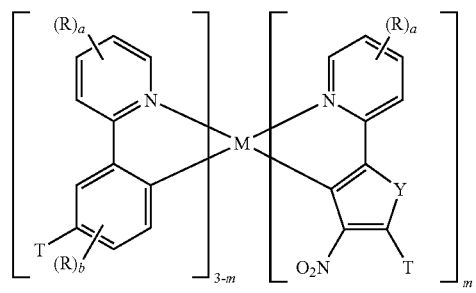
Compounds (7a)
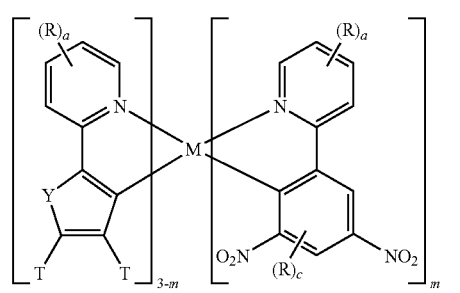
Compounds (8a)
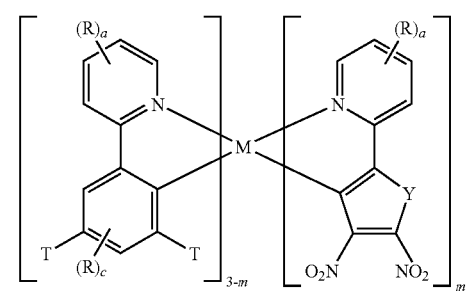
Compounds (17)
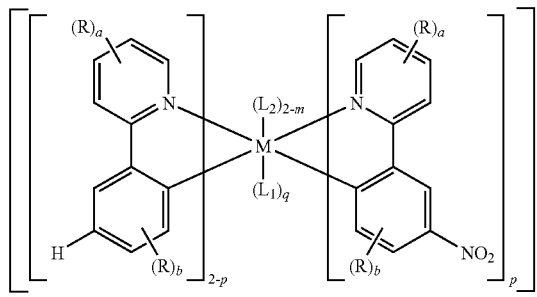
-continued
Compounds (18)
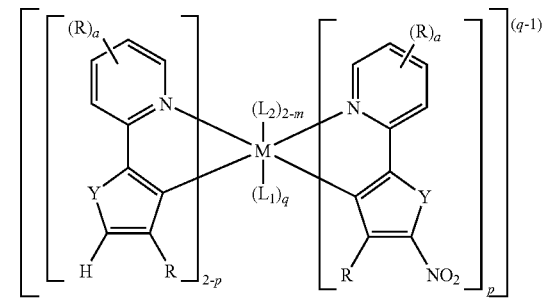
Compounds (19)
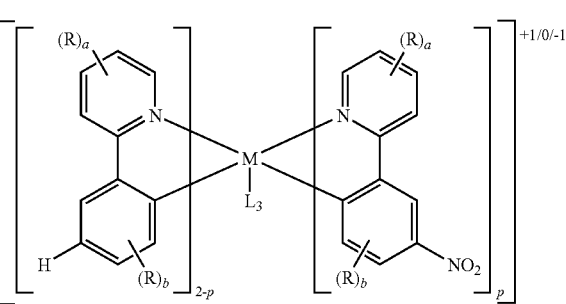
Compounds (20)
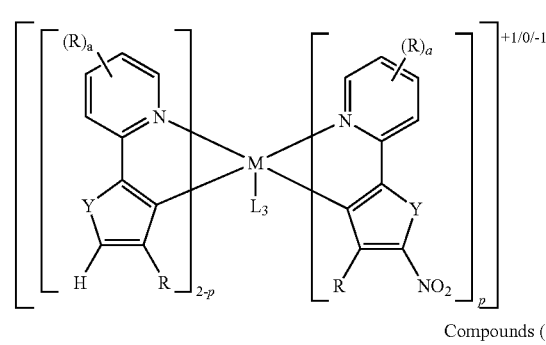
Compounds (21)
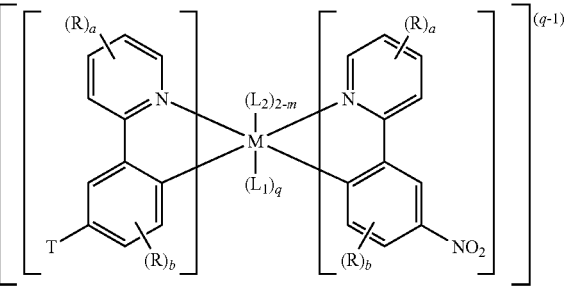
Compounds (22)
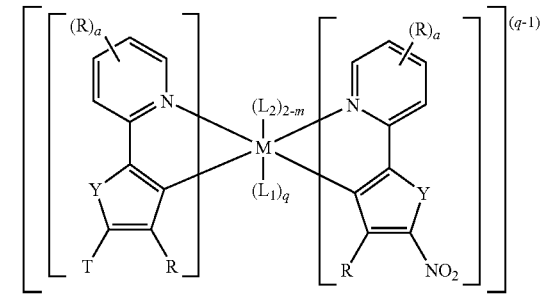

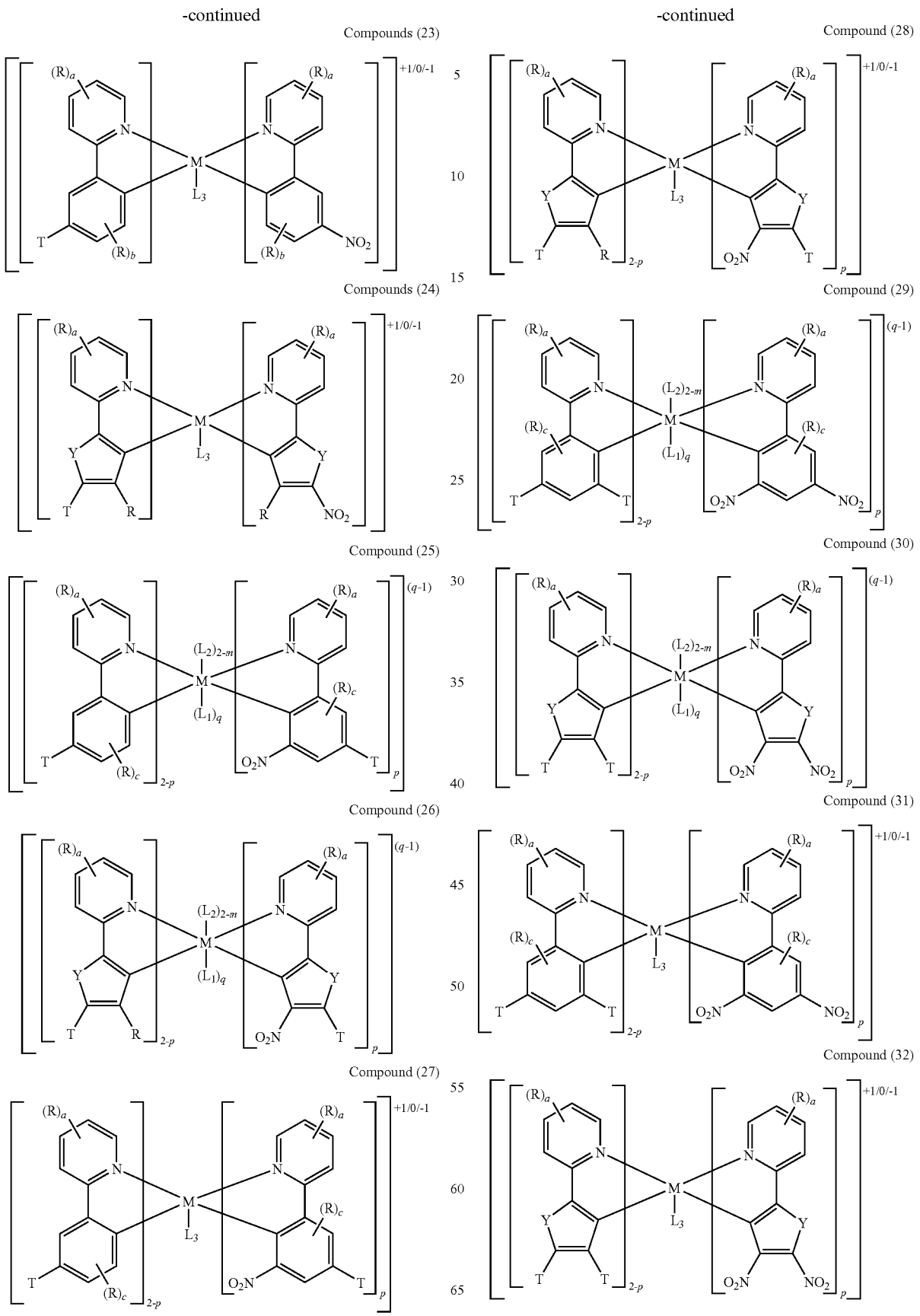

where the symbols and indices have the following meaning:

M denotes Rh, Ir;

Y denotes O, S, Se, $NR^1$;

Z is equal to F, Cl, Br, I, $O-R^1$, $S-R^1$, $N(R^1)_2$;

R is, identically or differently on each occurrence, H, F, Cl, Br, CN, a straight-chain or branched or cyclic alkyl or alkoxy group having from 1 to 20 C atoms, where one or more non-adjacent $CH_2$ groups may be replaced by —O—, —$SiR^1_2$—, —S—, —$NR^1$— or —$CONR^1$— and where one or more H atoms may be replaced by F, or an aryl or heteroaryl group having 4 to 14 C atoms, which may be substituted by one or more non-aromatic radicals R, where a plurality of substituents R, both on the same ring and also on the two different rings, may together in turn define a further aliphatic or aromatic, mono- or polycyclic ring system;

T is, identically or differently on each occurrence, F, Cl, Br, CN, a straight-chain or branched or cyclic alkyl or alkoxy group having from 1 to 20 C atoms, where one or more non-adjacent $CH_2$ groups may be replaced by —O—, —$SiR^1_2$—, —S—, —$NR^1$— or —$CONR^1$— and where one or more H atoms may be replaced by F, or an aryl or heteroaryl group having 4 to 14 C atoms, which may be substituted by one or more non-aromatic radicals R, where a plurality of substituents R, both on the same ring and also on the two different rings, may together in turn define a further aliphatic or aromatic, mono- or polycyclic ring system;

$R^1$ is, identically or differently on each occurrence, H or an aliphatic or aromatic hydrocarbon radical having 1 to 20 C atoms;

$L^1$ is a neutral, monodentate ligand;

$L^2$ is a monoanionic, monodentate ligand;

$L^3$ is a neutral or mono- or dianionic bidentate ligand;

a is 0, 1, 2, 3, or 4;

b is 0, 1, 2, or 3;

c is 0, 1, or 2;

m is 1 or 2;

n is 1, 2 or 3;

p is 1 or 2;

q is 0, 1 or 2;

by reaction of compounds (33) to (64) with a nitrating agent:

Compounds (33)

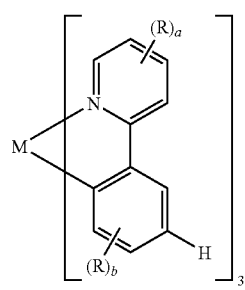

-continued

Compounds (34)

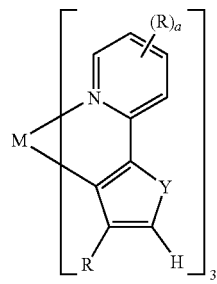

Compounds (35)

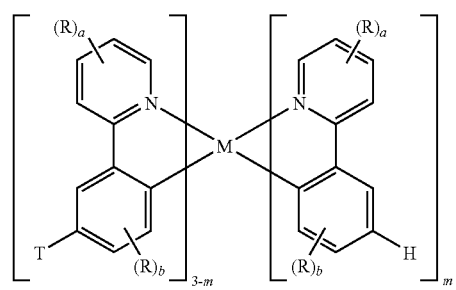

Compounds (36)

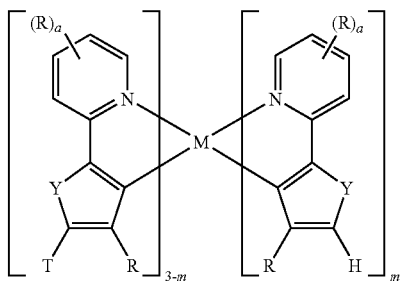

Compounds (37)

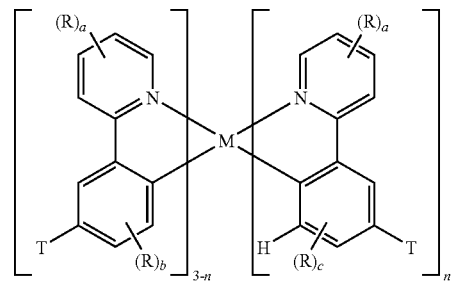

Compounds (38)

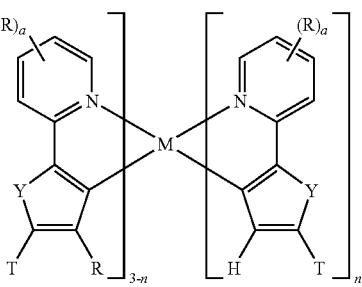

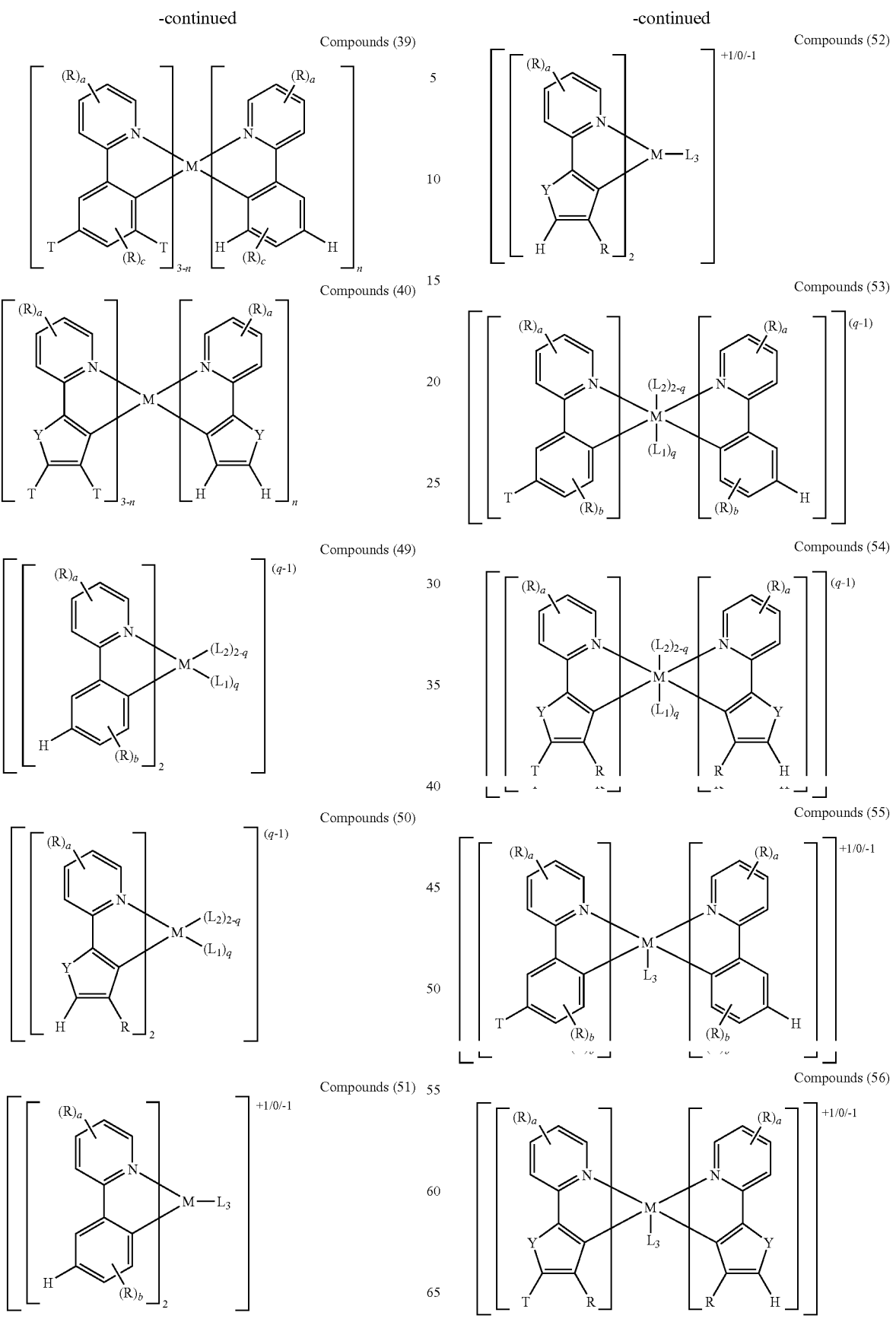

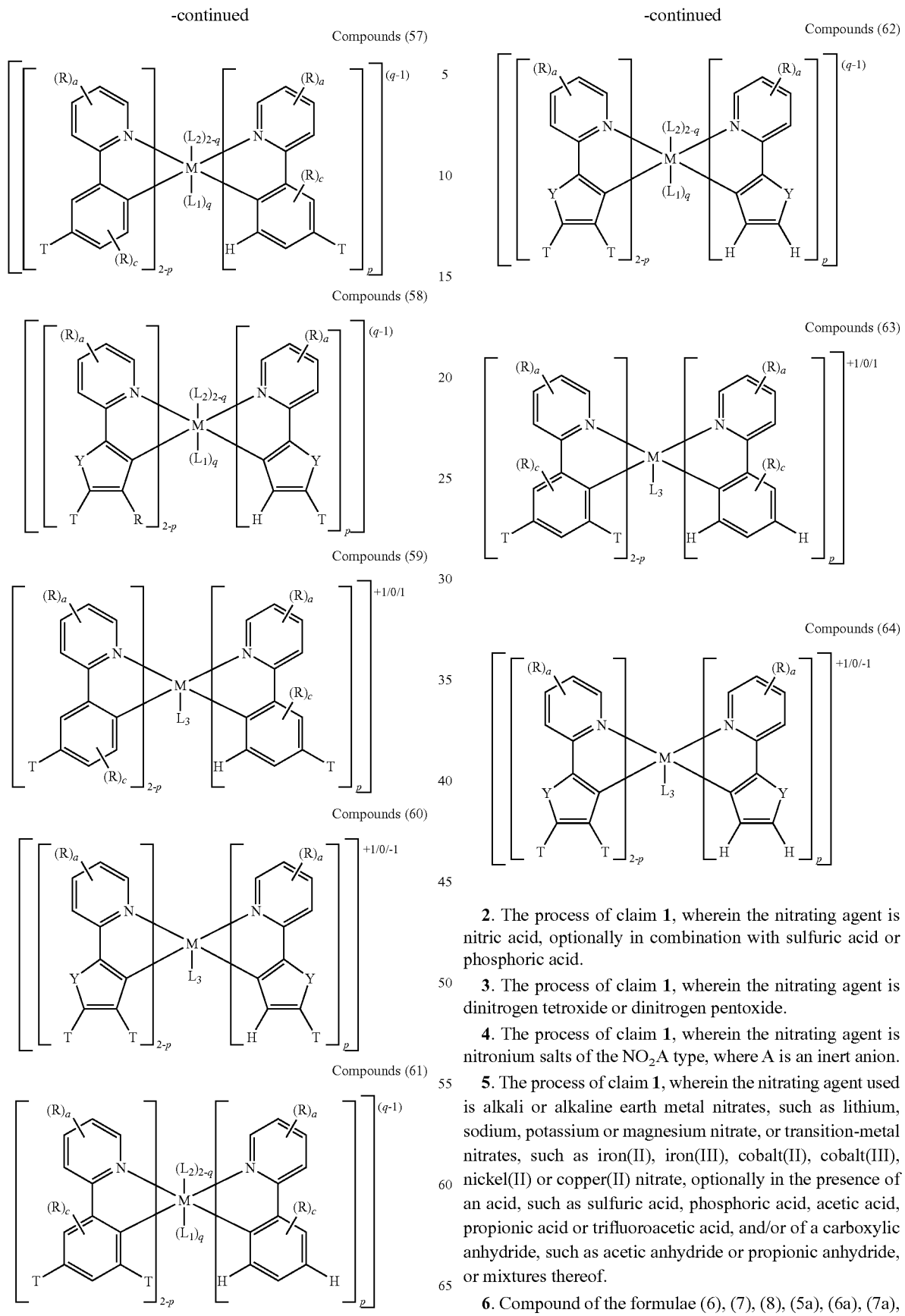

2. The process of claim 1, wherein the nitrating agent is nitric acid, optionally in combination with sulfuric acid or phosphoric acid.

3. The process of claim 1, wherein the nitrating agent is dinitrogen tetroxide or dinitrogen pentoxide.

4. The process of claim 1, wherein the nitrating agent is nitronium salts of the NO$_2$A type, where A is an inert anion.

5. The process of claim 1, wherein the nitrating agent used is alkali or alkaline earth metal nitrates, such as lithium, sodium, potassium or magnesium nitrate, or transition-metal nitrates, such as iron(II), iron(III), cobalt(II), cobalt(III), nickel(II) or copper(II) nitrate, optionally in the presence of an acid, such as sulfuric acid, phosphoric acid, acetic acid, propionic acid or trifluoroacetic acid, and/or of a carboxylic anhydride, such as acetic anhydride or propionic anhydride, or mixtures thereof.

6. Compound of the formulae (6), (7), (8), (5a), (6a), (7a), (8a), (25), (26), (27), (28), (29), (30), (31), and (32):

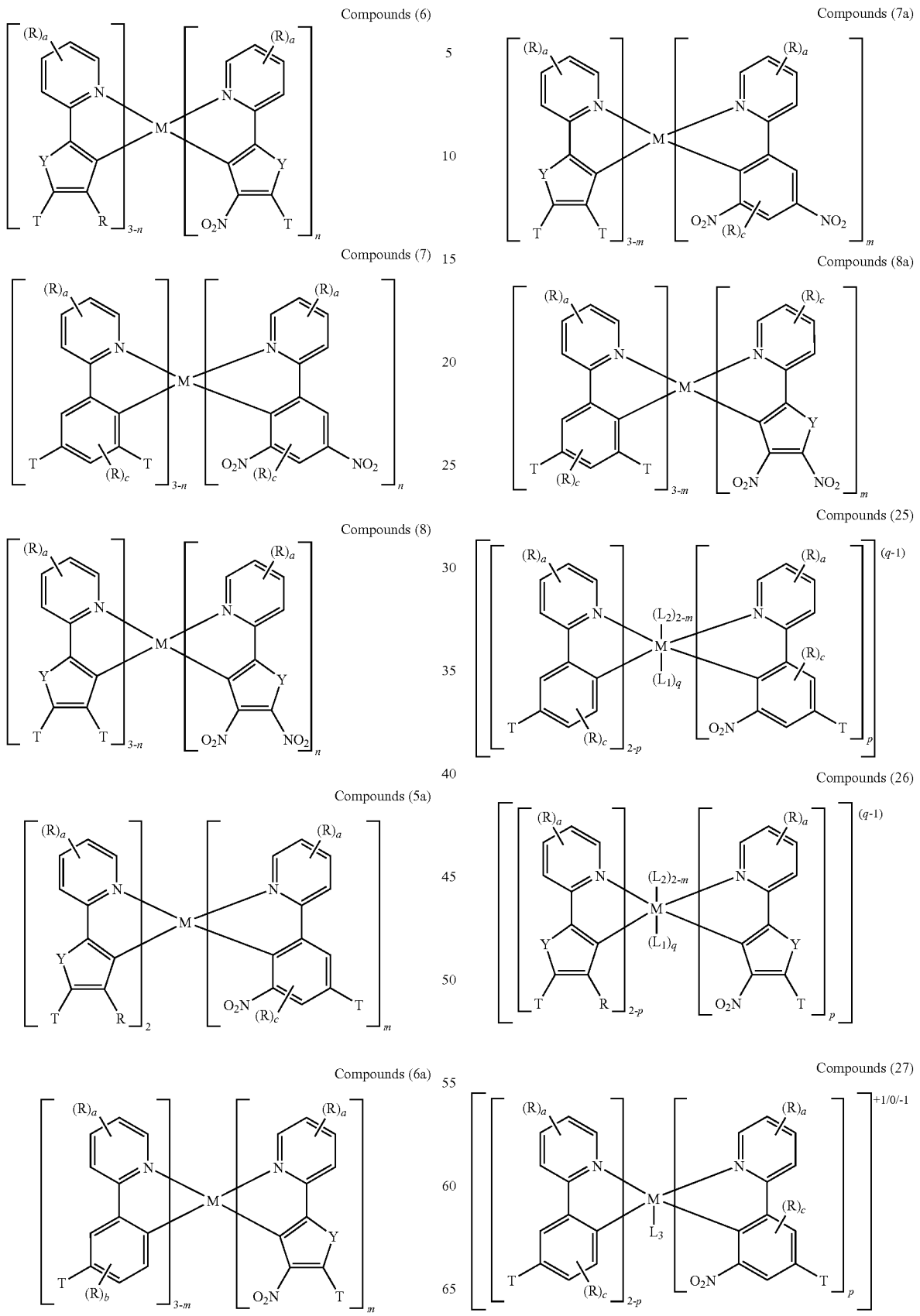

Compounds (28), Compounds (29), Compounds (30), Compounds (31), Compounds (32)

wherein:
M denotes Rh, Ir;
Y denotes O, S, Se, $NR^1$;
Z is equal to F, Cl, Br, I, O—$R^1$, S—$R^1$, N($R^1$)$_2$;
R is, identically or differently on each occurrence, H, F, Cl, Br, CN, a straight-chain or branched or cyclic alkyl or alkoxy group having from 1 to 20 C atoms, where one or more non-adjacent $CH_2$ groups may be replaced by —O—, —$SiR^1{}_2$—, —S—, —$NR^1$— or —$CONR^1$— and where one or more H atoms may be replaced by F, or an aryl or heteroaryl group having 4 to 14 C atoms, which may be substituted by one or more non-aromatic radicals R, where a plurality of substituents R, both on the same ring and also on the two different rings, may together in turn define a further aliphatic or aromatic, mono- or polycyclic ring system;
T is, identically or differently on each occurrence, F, Cl, Br, CN, a straight-chain or branched or cyclic alkyl or alkoxy group having from 1 to 20 C atoms, where one or more non-adjacent $CH_2$ groups may be replaced by —O—, —$SiR^1{}_2$—, —S—, —$NR^1$—, or —$CONR^1$— and where one or more H atoms may be replaced by F, or an aryl or heteroaryl group having 4 to 14 C atoms, which may be substituted by one or more non-aromatic radicals R, where a plurality of substituents R, both on the same ring and also on the two different rings, may together in turn define a further aliphatic or aromatic, mono- or polycyclic ring system;
$R^1$ is, identically or differently on each occurrence, H or an aliphatic or aromatic hydrocarbon radical having 1 to 20 C atoms;
$L^1$ is a neutral, monodentate ligand;
$L^2$ is a monoanionic, monodentate ligand;
$L^3$ is a neutral or mono- or dianionic bidentate ligand;
a is 0, 1, 2, 3, or 4;
b is 0, 1, 2, or 3;
c is 0, 1, or 2;
m is 1 or 2;
n is 1, 2 or 3;
p is 1 or 2;
q is 0, 1 or 2;
7. The compounds according to claim 6, wherein purity (determined by means of 1H-NMR or HPLC) is greater than 99%.

* * * * *

UNITED STATES PATENT AND TRADEMARK OFFICE
CERTIFICATE OF CORRECTION

PATENT NO.       : 7,589,203 B2                                    Page 1 of 1
APPLICATION NO.  : 10/532185
DATED            : September 15, 2009
INVENTOR(S)      : Stössel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1070 days.

Signed and Sealed this

Twenty-first Day of September, 2010

David J. Kappos
*Director of the United States Patent and Trademark Office*